(12) United States Patent
Thompson et al.

(10) Patent No.: US 8,916,697 B2
(45) Date of Patent: Dec. 23, 2014

(54) NUCLEIC ACID COMPLEXES

(71) Applicant: Purdue Research Foundation, West Lafayette, IN (US)

(72) Inventors: David H. Thompson, West Lafayette, IN (US); Aditya Kulkarni, West Lafayette, IN (US); Wei Deng, Shanghai (CN)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/826,887

(22) Filed: Mar. 14, 2013

(65) Prior Publication Data
US 2013/0261168 A1    Oct. 3, 2013

Related U.S. Application Data

(60) Provisional application No. 61/617,882, filed on Mar. 30, 2012.

(51) Int. Cl.
*C07H 21/04*       (2006.01)
*C12N 15/85*       (2006.01)
*C12N 15/87*       (2006.01)

(52) U.S. Cl.
CPC ...... *C12N 15/85* (2013.01); *C12N 2710/10043* (2013.01); *C12N 15/87* (2013.01)
USPC ........................................ 536/24.5; 536/23.1

(58) Field of Classification Search
None
See application file for complete search history.

(56) References Cited

U.S. PATENT DOCUMENTS

| | | | | |
|---|---|---|---|---|
| 2004/0009229 | A1* | 1/2004 | Unger et al. | 424/486 |
| 2010/0136129 | A1* | 6/2010 | Agueros Bazo et al. | 424/499 |
| 2012/0310140 | A1* | 12/2012 | Kramer et al. | 604/20 |

OTHER PUBLICATIONS

Mancuso, et al., "Gene therapy for red-green colour blindness in adult primates", Nature, 2009, 461, 784-8.
Waehler, et al. "Engineering targeted viral vectors for gene therapy" Nature Rev. Genet., 2007, 8, 573-587.
Semple, et al. "Rational design of cationic lipids for siRNA delivery", Nature Biotech, 2010, 20, 172-6.
Davis, et al. "Evidence of RNAi in humans from systemically administered siRNA via targeted nanoparticles", Nature, 2010, 464, 1067-70.
Nayak, et al. "Progress and Prospects: immune responses to viral vectors", Gene Ther., 2010.
Li, et al., "Non-viral is superior to viral gene delivery", J. Control. Rel. 2007, 123, 181-3.
Xu, et al., "Drug Delivery Trends in Clinical Trails and Translational Medicine: challenges and opportunities in the delivery of nucleic acid-based therapeutics", J. Pharm. Sci., 2011, 38-52.
Whitehead, et al., "Knocking down barriers:advances in siRNA delivery", Nature Rev. Drug. Disc. 2009, 8, 129.
Shan, et al. "In vitro macrophage uptake and in vivo biodistribution of long-circulation nanoparticles with poly(ethylene-glycol)-modified PLA (BAB type) triblock copolymer" Coll. Surfaces B: Bioint, 2009, 72, 303.
Gabizon, et al. "Liposome formulations with prolonged circulation time in blood and enhanced uptake by tumors", Proc. Natl. Acad. Sci. USA, 1988, 85, 6949.

* cited by examiner

*Primary Examiner* — Kimberly Chong
(74) *Attorney, Agent, or Firm* — Mark S. Cohen; Pearl Cohen Zedek Latzer Baratz LLP

(57) ABSTRACT

The invention relates to nucleic acid complexes, methods of preparation thereof, and uses thereof for delivering a nucleic acid into a cell.

22 Claims, 25 Drawing Sheets

NUCLEIC ACID COMPLEXES

CROSS REFERENCE TO RELATED APPLICATIONS

This application claims the benefit of U.S. Provisional Application Ser. No. 61/617,882, filed on Mar. 30, 2012, the disclosure of which is incorporated herein by reference in its entirety.

GOVERNMENT INTEREST STATEMENT

This invention was made with government support under GM087016 awarded by the National Institutes of Health. The government has certain rights in the invention.

TECHNICAL FIELD

The invention relates to nucleic acid complexes, methods of preparation thereof, and uses thereof for delivering a nucleic acid into a cell.

BACKGROUND OF THE INVENTION

Safe and efficient delivery of nucleic acid constructs to target cells has great potential for the treatment of genetic diseases (Mancuso, et al. *Nature*, 2009, 461, 784-8; Waehler, et al. *Nature Rev. Genet.*, 2007, 8, 573-587; Semple, et al. *Nature Biotech*, 2010, 20, 172-6; and Davis, et al. *Nature*, 2010, 464, 1067-70). However, the clinical success of this approach depends on the development of effective delivery vehicles with low toxicity. Viral and non-viral vectors both have been studied for this purpose, but suffer from several key limitations. Although efficient and persistent, viral vectors are challenged by issues of large-scale production, immunogenicity, and safety, whereas non-viral vectors are limited primarily by lack of efficiency. Nonetheless, non-viral nucleic acid delivery has attracted considerable attention due to its scalability and modest host immunogenicity compared to viral vectors (Nayak, et al. *Gene Ther.*, 2010, 464, 1067-70; Li, et al. *J. Control. Rel.* 2007, 123, 181-3; and Xu, et al. *J. Pharm. Sci.*, 2011, 38-52).

RNA interference (RNAi) is a post-transcriptional gene silencing mechanism arising from degradation or translation arrest of target RNA. The ability of 21-23 nucleotide RNAs (siRNA) to mediate RNAi in mammalian cells has enormous therapeutic potential for the treatment of viral infections, cancer and neurological disorders (Ryther, et al., *Gene Therapy* 2005, 12, 5). The use of siRNA has several advantages over conventional chemotherapy in that the high specificity nucleic acid drug acts "upstream" from chemotherapeutic agents conferring the ability to target any protein and the capacity to potentially evade drug resistance (Whitehead, et al., *Nature Rev. Drug. Disc.* 2009, 8, 129). Thus, there is an ongoing need for a safe and efficient delivery of siRNA specifically to target cells.

SUMMARY OF THE INVENTION

In one aspect, the present invention provides a nucleic acid complex comprising a to nucleic acid, a macrocyclic compound, and a pendant polymer, wherein the pendant polymer is modified with a hydrophobic group, and wherein the macrocyclic compound and the pendant polymer form a host:guest polymer complex. In some embodiments, the nucleic acid is siRNA or pDNA. In some embodiments, the nucleic acid is siRNA. In other embodiments, the hydrophobic group is a lipid.

In another aspect, the present invention provides a method for delivering a nucleic acid into a cell, the method comprising the step of bringing a nucleic acid complex comprising the nucleic acid into contact with the cell, wherein the nucleic acid complex comprises said nucleic acid, a macrocyclic compound, and a pendant polymer, wherein the pendant polymer is modified with a hydrophobic group, and wherein the macrocyclic compound and the pendant polymer form a host:guest polymer complex. In some embodiments, the nucleic acid is siRNA or pDNA. In some embodiments, the nucleic acid is siRNA. In other embodiments, the hydrophobic group is a lipid.

In yet another aspect, the present invention provides a pharmaceutical composition comprising the nucleic acid complex of the present invention to produce a pharmaceutical for delivering a nucleic acid into a cell.

The details of one or more embodiments of the invention are set forth in the accompanying description below. Other features, objects, and advantages of the invention will be apparent from the description and drawings, and from the claims.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
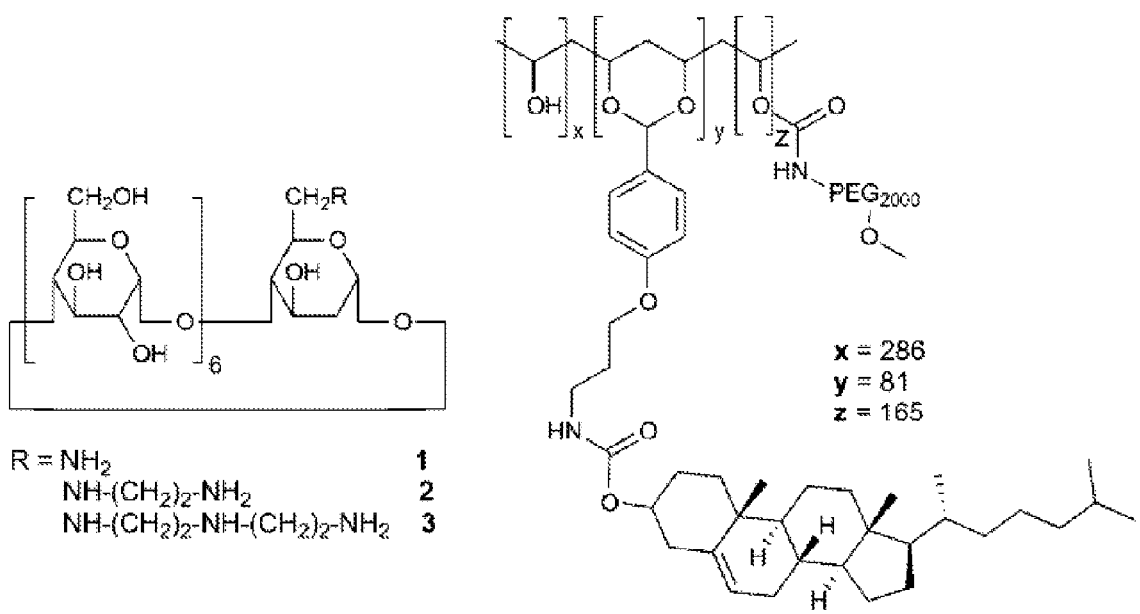
FIG. 1 depicts structures of amino-β-CDs 1, 2, 3 (left), Chol-PVA-PEG (right).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention provides a nucleic acid complex that comprises a nucleic acid, a macrocyclic compound, and a pendant polymer. In some embodiments, the pendant polymer is modified with a hydrophobic group, and the macrocyclic compound and the pendant polymer form a host:guest polymer complex. In some embodiments, the nucleic acid is siRNA or pDNA. In some embodiments, the nucleic acid is siRNA. In other embodiments, the nucleic acid is pDNA. In some embodiments, the hydrophobic group is a lipid.

In some embodiments, the macrocyclic compound is a modified cyclodextrin. In some embodiments, the modified cyclodextrin is a modified β-cyclodextrin comprising an amino moiety. In certain embodiments, the macrocyclic compound is mono-6-(amino)-6-deoxy-β-cyclodextrin, mono-6-(N,N'-dimethylethane-1,2-diamine)-6-deoxy-β-cyclodextrin, mono-6-(N'-(2-aminoethyl)ethane-1,2-diamine)-6-deoxy-β-cyclodextrin, hepta-6-(2'-aminoethyl)amino-β-cyclodextrin, hepta-6-(2'-hydroxyethylamino)-β-cyclodextri, or hepta-6-(hydrazino)-β-cyclodextrin.

In some embodiments, the pendant polymer comprises a poly(vinyl alcohol), polysaccharide, polyester, or polyamide backbone.

In some embodiments, the pendant polymer comprises a poly(vinyl alcohol) backbone.

In some embodiments, the pendant polymer comprises a poly(ethylene glycol) pendant group.

In some embodiments, the hydrophobic group is cholesterol, or a derivative or analog thereof. In some embodiments, the cholesterol, or a derivative or analog thereof, is linked through an acetal linkage to the backbone of the pendant polymer.

In some embodiments, the host:guest polymer complex condenses the nucleic acid to form a nanoparticle in a size of from about 120 nm to about 170 nm.

In some embodiments, the nucleic acid that can be condensed to form a nucleic acid complex of the present invention includes, but is not limited to, siRNA, mRNA, tRNA, rRNA, cDNA, miRNA (microRNA), ribozymes, antisense oligonucleotides, decoy oligonucleotides, plasmid DNA (pDNA), peptide nucleic acids, triplex-forming oligonucleotides (TFOs), aptamers, genes, or a derivative or analog thereof, or a combination thereof. In some embodiments, the nucleic acid is siRNA or pDNA. In other embodiments, the nucleic acid is pDNA. In some embodiments, the nucleic acid is siRNA. In other embodiments, the nucleic acid is a gene. The nucleic acid used in the nucleic acid complex of the present invention may be derived from humans, animals, plants, bacteria, viruses, or the like. In some embodiments, the nucleic acid may be synthesized either chemically or enzymatically. The nucleic acid for the nucleic acid complex of the invention may be single-stranded, double-stranded, or triple-stranded.

In some embodiments, the term "siRNA" refers to a small interfering RNA. In some embodiments, the siRNA comprises a duplex, or double-stranded region, of about 18-25 nucleotides long; often the siRNA contains from about two to four unpaired nucleotides at the 3' end of each strand. At least one strand of the duplex or double-stranded region of a siRNA is substantially homologous to, or substantially complementary to, a target RNA molecule. The siRNA may also contain additional sequences. Examples of such sequences include linking sequences, or loops, as well as stem and other folded structures.

In some embodiments, a "macrocyclic compound" can be a cyclic macromolecule or a macromolecular cyclic portion of a molecule. The macrocyclic compound can be a porphyrin or an analog or derivative thereof. The macrocyclic compound can be a polyether macrocycle, an analog or derivative, or a combination thereof, for example, a crown ether (e.g., benzo[24]crown-8). In some embodiments, the macrocyclic compound can be a calixarene, heterocalixarene, cucurbituril, or an analog or derivative or a combination thereof. In certain embodiments, the macrocyclic compound can be a modified calixarene, heterocalixarene, or cucurbituril. In some embodiments, the macrocyclic compound is a modified cucurbituril. In other embodiments, the macrocyclic compound is a modified calixarene. The macrocyclic compound can be a cyclic oligosaccharide, for example, cyclodextrin (CD). In some embodiments, the "cyclodextrin" can be composed of glucose monomers coupled together to form a conical, hollow molecule with a cavity. The cyclodextrin can be any suitable cyclodextrins, including alpha-, beta-, and gamma-cyclodextrins, and their combinations, analogs, and derivatives. The cyclodextrin can be either natural or modified. In some embodiments, the cyclodextrin can be modified with a functional group. In some embodiments, the cyclodextrin can be modified with an amino moiety. An amino moiety can refer to a moiety containing an amino group or a derivative thereof, which can be a primary amine, a secondary amine, or a tertiary amine moiety, or a combination thereof.

In some embodiments, the macrocyclic compound can be a modified α-cyclodextrin or β-cyclodextrin. In other embodiments, the macrocyclic compound can be a modified β-cyclodextrin. The modified β-cyclodextrin can contain an amino moiety. In some embodiments, the modified β-cyclodextrin is mono-6-(amino)-6-deoxy-β-cyclodextrin. In some embodiments, the modified β-cyclodextrin is mono-6-(N,N'-dimethylethane-1,2-diamine)-6-deoxy-β-cyclodextrin. In other embodiments, the modified β-cyclodextrin is mono-6-(N'-(2-aminoethyl)ethane-1,2-diamine)-6-deoxy-β-cyclodextrin. In some embodiments, the modified β-cyclodextrin is hepta-6-(2'-aminoethyl)amino-β-cyclodextrin. In certain embodiments, the modified β-cyclodextrin is hepta-6-(2'-hydroxyethylamino)-β-cyclodextrin. In other embodiments, the modified β-cyclodextrin is hepta-6-(hydrazino)-β-cyclodextrin.

In some embodiments, the macrocyclic compound may be suitable as a "guest" compound capable of forming a host:guest polymer complex with a polymer. In other embodiments, the macrocyclic compound may have "host" functionality. Exemplified macrocyclic compounds that have host functionality includes, but are not limited to, cyclodextrins, cavitands, crown ethers, cryptands, cucurbiturils, calixarenes, spherands, and the like.

In some embodiments, the pendant polymer is a polymer that has a chemical group being pendant from the backbone of the pendant polymer. The polymer backbone or main chain may be a substantially linear polymer. For example, it can be a long-chain carbon molecule, optionally substituted with nitrogen atoms or oxygen atoms. The backbone of the pendant to polymer can be a homopolymer or copolymer. In some embodiments, the polymer backbone or main chain can be a homopolymer. In some embodiments, a "homopolymer" is a polymer where only one type of monomers is used. Examples of homopolymers include, but are not limited to, poly(vinyl alcohol), poly(meth)acrylic acid, polyacrylamide, poly(ethylene oxide), poly(propylene oxide), poly(ethylene glycol), polyisoprene, poly(propylene glycol), poly(vinyl methyl ether), polyethylene, polypropylene, polyisobutylene, polybutadiene, polyureas, polysulfides, polydimethylsiloxane, polysaccharides (e.g., hyaluronic acid and pullulan), and polyesters. In some embodiments, the pendant polymer backbone may be selected from the group consisting of poly(vinyl alcohol), poly(ethylene glycol), poly(propylene glycol), polydimethylsiloxane, polyethylene, polypropylene, hyaluronic acid, and pullulan.

In some embodiments, the backbone or main chain of the pendant polymer can be a copolymer. A "copolymer" can be called "heteropolymer." In some embodiments, a copolymer refers to a polymer derived from two or more monomeric species. It can be a block copolymer, which includes two or more chemically distinct homopolymer blocks linked by covalent bonds. The block copolymer can be a diblock copolymer, a triblock copolymer, or a block copolymer with more than three distinct blocks. For example, it can be poly(vinyl alcohol)-poly(ethylene glycol) diblock copolymer or poly(ethylene glycol)-poly(vinyl alcohol)-poly(ethylene glycol) triblock copolymer. In some embodiments, the polymer backbone can be a polyester, for example, a polyester diblock copolymer. In certain embodiments, the polymer backbone is polyserine-PEG. In other embodiments, the polymer backbone is poly(lactic-b-glycolic acid). In some embodiments, the polymer backbone of the pendant polymer is a polyamide, for example, a polyamide diblock copolymer. In certain embodiments, the polymer backbone is a peptide-PEG diblock copolymer. The peptide-PEG diblock copolymer can be a repeating tripeptide block that terminates in a PEG2000 with a 6-mer, 9-mer, or 12-mer peptide segment.

In some embodiments, the polymer backbone of the pendant polymer comprises poly(vinyl alcohol). In some embodiments, the polymer backbone of the pendant polymer is a poly(vinyl alcohol) homopolymer. In other embodiments, the polymer backbone of the pendant polymer is a copolymer comprising a poly(vinyl alcohol) monomer. In some embodiments, the polymer backbone of the pendant polymer is a polysaccharide, polyester, or polyamide. In some embodiments, the polymer backbone of the pendant polymer is hyaluronic acid. In other to embodiments, the polymer backbone of the pendant polymer is pullulan. In other embodiments, the polymer backbone of the pendant polymer is a peptide-PEG diblock copolymer. In certain embodiments, the peptide-PEG diblock copolymer can be a repeating tripeptide block that terminates in a PEG2000 with a 6-mer, 9-mer, or 12-mer peptide segment.

A pendant polymer can comprise one or more pendant groups. The term "pendant" can be referred to one or more groups covalently bound to the backbone or main chain of a pendant polymer. The pendant groups suitable for use in various embodiments can be either reactive (e.g., carboxyl groups) or generally non-reactive (e.g., unsubstituted, saturated alkyl groups). In some embodiments, the pendant group can be selected from the group consisting of poly(vinyl alcohol), poly(meth)acrylic acid, polyacrylamide, poly(ethylene oxide), poly(propylene oxide), poly(ethylene glycol), polyisoprene, poly(propylene glycol), poly(vinyl methyl ether), polyethylene, polypropylene, polyisobutylene, polybutadiene, polyureas, polysulfides, and polydimethylsiloxane. In some embodiments, the pendant group can be poly(vinyl alcohol), poly(ethylene glycol), poly(propylene glycol), polydimethylsiloxane, polyethylene, or polypropylene. In certain embodiments, the pendant group can be polyethylene. In other embodiments, the pendant group can be poly(ethylene glycol). In some embodiments, the pendant polymer of the nucleic acid complex of the invention comprises two distinct pendant groups. In other embodiments, the pendant polymer of the nucleic acid complex of the invention comprises more than two distinct pendant groups, for example, three distinct pendant groups.

In some embodiments, the pendant polymer in the present invention is capable of forming a host:guest polymer complex with the macrocyclic compound of the invention via non-covalent bonding interactions. The non-covalent bonding interactions may include, but are not limited to, van der Waals forces, hydrogen bonding, dipole-dipole interactions, and ion-pairing interactions. In some embodiments, the host:guest polymer complex includes a macrocyclic compound and a guest pendant group in a molar ratio of about 1:3. In some embodiments, the host:guest polymer complex includes a macrocyclic compound and a guest pendant group in a molar ratio of about 1:2. In other embodiments, the host:guest polymer complex includes a macrocyclic compound and a guest pendant group in a molar ratio of about 1:1. In some embodiments, the host:guest polymer complex includes a macrocyclic compound and a guest pendant group in a molar ratio of about 2:1. In certain embodiments, the host:guest polymer complex includes a macrocyclic compound and a guest pendant group in a molar ratio of about 3:1. In some embodiments, the "host:guest polymer complex" refers to a host:guest pendant polymer complex as indicated in the Examples of the present application.

The host or guest functionality of a pendant polymer may be part of the polymer backbone, or present as an end-group, or may be present in one or more pendant groups. In some embodiments, the pendant group of the pendant polymer can have guest functionality. Examples of a pendant polymer having guest functionality in its pendant groups include, but are not limited to, a polymer having pendant adamantane groups, diadamantane groups, naphthalene groups, and cholesterol groups, or derivatives or analogs thereof.

In some embodiments, the pendant group of a pendant polymer may be water soluble, thus making the pendant polymer water soluble. Examples of water-soluble polymers include, but are not limited to, polyethylene glycol, copolymers of polyethylene glycol and polypropylene glycol, carboxymethyl cellulose, dextran, polyvinylpyrrolidone, and polyproline, or a combination thereof. In some embodiments, the pendant group is a poly(ethylene glycol) polymer.

In some embodiments, the pendant polymer can be modified to attach another group that has guest functionality to form a host:guest polymer complex with a compound having host functionality. In some embodiments, the attached group having guest function can be a hydrophobic group, or a derivative or analog thereof. The presence of a hydrophobic group, or a derivative or analog thereof, may promote disruption of biological membranes to facilitate intracellular delivery of the nucleic acid complex of the invention. Thus, a hydrophobic pendant group may serve as a guest compound for a host:guest polymer complex and help transport a nucleic acid into a cell by further forming a nucleic acid complex with the nucleic acid. In some embodiments, the hydrophobic group is adamantane. In other embodiments, the hydrophobic group is a drug molecule, or a derivative or analog thereof, which is capable of forming a host:guest complex. In some embodiments, the hydrophobic group is a lipid. The lipid includes, but is not limited to, (1) uncharged lipid components, for example, cholesterol, ceramide, diacylglycerol, acyl(poly ethers) or alkylpoly(ethers); (2) neutral phospholipids, for example, diacylphosphatidylcholines, sphingomyelins, and diacylphosphatidylethanolamines, (3) anionic lipids, for example, diacylphosphatidylserine, diacylphosphatidylglycerol, diacylphosphatidate, cardiolipin, diacylphosphatidylinositol, diacylglycerolhemisuccinate, diacyglycerolhemigluratate, cholesterylhemisuccinate, cholesterylhemiglutarate, and the like; (4) polymer-conjugated lipids, for example, N-[methoxy-(poly(ethylene glycol)diacylphosphatidylethanolamine, poly(ethylene glycol)-diacylglycerol, poly(ethylene glycol)-ceramide; and (5) cationic lipids, for example, 1,2,-diacyl-3-trimethylammonium-propane (DOTAP), dimethyldioctadecylammonium bromide (DDAB), and 1,2-diacyl-sn-glycero-3-ethylphosphocholine. In some embodiments, the lipid is cholesterol. In other embodiments, the lipid is a phospholipid. In certain embodiments, the lipid is an anionic lipid, for example, cholesterolhemiglutarate.

In some embodiments, the hydrophobic group can be attached to the polymer backbone or main chain through a linkage. In some embodiments, the linkage can be designed to be easily broken, thus removing the hydrophobic group from the polymer backbone under certain conditions. In some embodiments, the linkage can be acid-labile. For example, the linkage can be an acetal or ketal moiety. For example, benzylidene or acetonide (isopropylidene). As a result, the acetal linkage or the ketal linkage can be cleaved under acidic conditions. In some embodiments, the linkage is an acetal moiety. In certain embodiments, the acetal moiety is benzylidene or its derivatives.

In some embodiments, the hydrophobic group is attached to the polymer backbone of a pendant polymer through a benzylidene linkage. Such a linkage can be cleaved under acidic conditions. In some embodiments, a hydrophobic group is attached to the backbone of a pendant polymer via the benzylidene linkage. In certain embodiments, the hydrophobic group is cholesterol. In other embodiments, the hydrophobic group is adamantane. In certain embodiments, the hydrophobic group is a drug molecule.

In some embodiments, a large pendant group of the pendant polymer in the nucleic acid complex may help stabilize the nucleic acid complex in the presence of serum. In certain embodiments, the pendant group of the pendant polymer can have an average molecular weight of from about 250 Da to about 3000 Da. In some embodiments, the pendant group of the pendant polymer can have an average molecular weight of about 250 Da or less. In certain embodiments, the pendant group of the pendant polymer can have an average molecular weight of from about 250 Da to about 750 Da. In some embodiments, the pendant group of the pendant polymer can have an average molecular weight of from about 500 Da to about 750 Da. In certain embodiments, the pendant group of the pendant polymer can have an average molecular weight of about 750 Da. In other embodiments, the pendant group of the pendant polymer can have an average molecular weight of from about 750 Da to about 3000 Da. In some embodiments, the pendant group of the pendant polymer can have an average molecular weight of from about 750 Da to about 1000 Da. In some embodiments, the pendant group of the pendant polymer can have an average molecular weight of from about 1000 Da to about 3000 Da. In some embodiments, the pendant group of the pendant polymer can have an average molecular weight of from about 1000 Da to about 2000 Da. In certain embodiments, the pendant group of the pendant polymer can have an average molecular weight of about 2000 Da. In some embodiments, the pendant group of the pendant polymer can have an average molecular weight of from about 2000 Da to about 3000 Da. In certain embodiments, the pendant group of the pendant polymer can have an average molecular weight of about 3000 Da or more.

In some embodiments, the backbone of the pendant polymer in the nucleic acid complex of the invention can have an average molecular weight of about 27 kDa. In some embodiments, the backbone of the pendant polymer can have an average molecular weight of about 10 kDa or less. In other embodiments, the backbone of the pendant polymer can have an average molecular weight of from about 10 kDa to about 40 kDa. In some embodiments, the backbone of the pendant polymer can have an average molecular weight of from about 20 kDa to about 40 kDa. In certain embodiments, the backbone of the pendant polymer can have an average molecular weight of about 30 kDa to about 40 kDa. In some embodiments, the backbone of the pendant polymer can have an average molecular weight of about 40 kDa or more.

In some embodiments, the "average molecular weight" can refer to the weight average molecular weight (Mw) that can be calculated by $$Mw=\Sigma N_i M_i^2/\Sigma N_i M_i$$

where $N_i$ is the number of molecules of molecular weight $M_i$.

The molar ratio between the amine nitrogen in the functionalized macrocyclic compound and the phosphate in the nucleic acid (N:P ratio) may affect the degree to which the nucleic acid may be condensed into a nucleic acid complex. In some embodiments, the molar ratio of the amine nitrogen in the macrocyclic compound to the phosphate in the nucleic acid is from about 0.1:1 to about 100:1. In some embodiments, the molar ratio of the amine nitrogen in the macrocyclic compound to the phosphate in the nucleic acid is from about 1:1 to about 50:1. In some embodiments, the molar ratio of the amine nitrogen in the macrocyclic compound to the phosphate in the nucleic acid is from about 1:1 to about 40:1. In some embodiments, the molar ratio of the amine nitrogen in the macrocyclic compound to the phosphate in the nucleic acid is from about 1:1 to about 5:1. In other embodiments, the molar ratio of the amine nitrogen in the macrocyclic compound to the phosphate in the nucleic acid is from about 5:1 to about 40:1. In other embodiments, the molar ratio of the amine nitrogen in the macrocyclic compound to the phosphate in the nucleic acid is from about 5:1 to about 30:1. In certain embodiments, the molar ratio of the amine nitrogen in the macrocyclic compound to the phosphate in the nucleic acid is from about 5:1 to about 20:1. In certain embodiments, the molar ratio of the amine nitrogen in the macrocyclic compound to the phosphate in the nucleic acid is from about 10:1 to about 20:1.

In some embodiments, the backbone of the pendant polymer, bearing a pendant group, in the nucleic acid complex of the invention is modified by attachment to a hydrophobic group. The molar ratio of the hydrophobic group to the pendant group can be from about 10:1 to about 0.1:1, or from about 10:1 to about 0.2:1, or from about 10:1 to about 0.3:1, or from about 10:1 to about 0.5:1. The molar ratio of the hydrophobic group to the pendant group can be from 5:1 to about 0.1:1, or from about 5:1 to about 0.2:1, or from about 5:1 to about 0.3:1, or from about 5:1 to about 0.5:1. The molar ratio of the hydrophobic group to the pendant group can be from about 2:1 to about 0.5:1. The molar ratio of the hydrophobic group to the pendant group can be from 2:1 to about 0.3:1, or from about 2:1 to about 0.2:1, or from about 2:1 to about 0.1:1. The molar ratio of the hydrophobic groups to the pendant group can be from 1:1 to about 0.5:1, or from about 1:1 to about 0.3:1, or from about 1:1 to about 0.5:1, or from about 1:1 to about 0.1:1.

As will be appreciated in the art, when the components of the nucleic acid complex of the present invention, including a nucleic acid, a macrocyclic compound, and a pendant polymer, produce a neutral or slightly negatively-charged complex, the formed nucleic acid complex constitutes a desired combination of these components. The surface charge of the nucleic acid complex of the invention can be determined by zeta potential measurements. The nucleic acid complex of the present invention, in some embodiments, has a surface charge that is slightly negative, for example, a zeta potential of from about −20 mV to about 0 mV. In other embodiments, the nucleic acid complex of the invention has a surface charge of from about −15 mV to about 0 mV. In certain embodiments, the nucleic acid complex of the invention has a surface charge of from about −10 mV to about 0 mV. In certain embodiments, the nucleic acid complex of the invention has a surface charge of from about −5 mV to about 0 mV. In other embodiments, the nucleic acid complex produces nearly neural surface charges. In certain embodiments, when the surface charge of the nucleic acid complex is about neural, the N:P ratio is about 20. In some embodiments, when the surface charge of the nucleic acid complex is about neural, the N:P ratio is from about 5 to about 20. In certain embodiments, when the surface charge of the nucleic acid complex is about neural, the N:P ratio is from about 5 to about 10. In other embodiments, when the surface charge of the nucleic acid complex is about neural, the N:P ratio is from about 10 to about 20.

In one aspect, the present invention provides a pharmaceutical composition comprising the nucleic acid complex of the invention to produce a pharmaceutical for delivering a nucleic acid into a cell.

In some embodiments, the pharmaceutical composition comprises a pharmaceutically effective amount of the nucleic acid complex and one or more pharmaceutically acceptable carriers. The pharmaceutical composition may include one or additional therapeutic agents.

The pharmaceutical composition of the invention may be formulated in a variety of ways, including, for example, solid, semi-solid, and liquid dosage forms, such as liquid solutions, dispersions or suspensions, tablets, pills, powders, liposomes, micelles, nanoparticles, and suppositories. In some embodiments, the composition is in the form of injectable or infusible solutions.

In some embodiments, the pharmaceutical composition of the present invention may contain various additives such as isotonizing agents, excipients, diluents, thickeners, stabilizers, buffers, and preservatives. The amounts of such additives can be suitably selected according to the form of use of the nucleic acid complex composition.

In some embodiments, the pharmaceutical composition can include a pharmaceutically acceptable filler excipient. A wide variety of excipients may be utilized as fillers for inclusion in compositions containing the nucleic acid complex of the invention. For example, examples of the filler excipient may include, but is not limited to, sugars, sugar alcohols, starches, celluloses, and combinations thereof. In some embodiments, the filler excipient can include lactose, sucrose, trehalose, dextrose, galactose, mannitol, maltitol, maltose, sorbitol, xylitol, mannose, glucose, fructose, polyvinyl pyrrolidone, glycine, maltodextrin, hydroxymethyl starch, gelatin, sorbitol, ficol, sodium chloride, calcium phosphate, calcium carbonate, polyethylene glycol, and combinations thereof. In some embodiments, the filler excipient can be sucrose. In certain embodiments, the filler excipient can be lactose.

It is an important aspect of the present invention to prepare a nucleic acid complex including a nucleic acid, a macrocyclic compound, and a pendant polymer.

The present invention, in some embodiments, provides a method of preparing a nucleic acid complex including a nucleic acid, a macrocyclic compound, and a pendant polymer, comprising the steps of (a) contacting the macrocyclic compound with the pendant polymer to form a host:guest polymer complex; and (b) condensing the host:guest polymer complex with the nucleic acid to form the nucleic acid complex.

The macrocyclic compound can be prepared by means known in the art. In some embodiments, the macrocyclic compound can be synthesized as exemplified in Examples 1-5 and 14-16.

The pendant group of a pendant polymer can be preformed within the polymer structure through choice of suitable reactive monomers. Alternatively, after a substantially linear polymer, e.g., the backbone of a pendant polymer, is formed, it can be attached to a pendant group. In some embodiments, the pendant polymer can be further modified to link a group, e.g., a hydrophobic group, which may have host and/or guest functionality. In other embodiments, the backbone of a pendant polymer can be modified to link a lipid group, followed by attachment of a pendant group to the backbone of the pendant polymer, thus yielding a pendant polymer bearing both a lipid group and a pendant group. In some embodiments, the lipid group may refer to another pendant group as indicated in the Examples of the present application.

In some embodiments, the hydrophobic group can be linked to the polymer backbone via an acetal linkage, and the pendant group can be attached to the polymer backbone by a relatively stable covalent bond under acidic conditions. Thus, under an acidic condition, the acetal linkage may be destroyed thus releasing the hydrophobic group from the linkage to the backbone of the pendant polymer, while the pendant group may stay with the polymer backbone.

For a pendant polymer having a lipid group and a pendant group, it can be prepared by treatment of the backbone polymer with an aldehyde when an acetal is a linkage to the lipid group, followed by addition of a compound containing the lipid group. Subsequently, the pendant group can be connected to the backbone of the pendant polymer by reactions known in the art.

The host:guest polymer complex can be synthesized in a variety of ways, for example, by combining the pendant polymer and the macrocyclic compound in water or an aqueous solution. The pendant polymer and the macrocyclic compound can self-assemble to form a non-covalent host:guest polymer complex. The self-assembling of the pendant polymer and the macrocyclic compound may take place at about 20° C. In some embodiments, the formation of the pendant polymer complex may take place at about 20° C. or lower. In some embodiments, the formation of the host:guest polymer complex may take place at an elevated temperature, for example, from about 20° C. to about 70° C., or from about 20° C. to about 50° C. In some embodiments, the temperature can be from about 50° C. to about 70° C. In certain embodiments, the temperature can be about 70° C. or higher.

In some embodiments, the host:guest polymer complex can be isolated and purified and then is stored ready for the next reaction steps. In some embodiments, it is not necessary to isolate or purify the host:guest polymer complex from reaction mixtures. The host:guest polymer complex can be used for next steps upon formation.

The host:guest polymer complex can form a nucleic acid complex with a nucleic acid via multivalent electrostatic interactions. In some embodiments, the host:guest polymer complex is capable of condensing a nucleic acid into compact and uniform spherical particles.

In some embodiments, the nucleic acid complex of the present invention can be in the form of nanoparticles. In some embodiments, the size of the nanoparticles can be about 100 nm or less. In other embodiments, the size of the nanoparticles can range from about 100 nm to about 200 nm. In some embodiments, the size of the nanoparticles can range from about 100 nm to about 120 nm. In other embodiments, the size of the nanoparticles can range from about 120 nm to about 200 nm. In some embodiments, the size of the nanoparticles can range from about 120 nm to about 150 nm. In other embodiments, the size of the nanoparticles can range from about 150 nm to about 200 nm. In certain embodiments, the size of the nanoparticles can range from about 150 nm to about 170 nm. In other embodiments, the size of the nanoparticles can range from about 170 nm to about 200 nm. In certain embodiments, the size of the nanoparticles can be about 200 nm or greater.

In some embodiments, the size of the nanoparticles can range from about 200 nm to about 5500 nm. In some embodiments, the size of the nanoparticles can range from about 200 nm to about 4000 nm. In some embodiments, the size of the nanoparticles can range from about 200 nm to about 3000 nm. In some embodiments, the size of the nanoparticles can range from about 200 nm to about 2000 nm. In some embodiments, the size of the nanoparticles can range from about 200 nm to about 1000 nm. In some embodiments, the size of the nanoparticles can range from about 200 nm to about 500 nm. In some embodiments, the size of the nanoparticles can range from about 200 nm to about 400 nm. In some embodiments, the size of the nanoparticles can range from about 200 nm to about 300 nm. In some embodiments, the size of the nanoparticles can range from about 200 nm to about 250 nm.

In another aspect, the present invention provides a method of preparing a nucleic acid complex including a nucleic acid, a macrocyclic compound, and a pendant polymer, comprising the steps of (a) contacting the nucleic acid with the macrocyclic compound to form an intermediate nucleic acid complex;

and (b) condensing the intermediate nucleic acid complex with the pendant polymer to form the nucleic acid complex.

In some embodiments, mixing a nucleic acid, for example, siRNA, with a macrocyclic compound at 25° C. can lead to the formation of an intermediate nucleic acid complex. In other embodiments, the formation of the nucleic acid complex can be achieved at about 0° C. or at a temperature between −10° C. and 60° C., for example, at about 20° C. In certain embodiments, the temperature is below 0° C., for example, about −5° C. or about −10° C. In some embodiments, the temperature is from about −10° C. to about 0° C. In some embodiments, the temperature is from about 0° C. to about 45° C. In other embodiments, the temperature is from about 0° C. to about 20° C. In certain embodiments, the temperature is from about 20° C. to about 45° C. In some embodiments, the temperature is from about 45° C. to about 60° C. In certain embodiments, the temperature is about 60° C. or above. In some embodiments, the mixing of a nucleic acid and a macrocyclic compound can be conducted in water or an aqueous solution. The intermediate nucleic acid can further complexed with a pendant polymer to form a nucleic acid complex of the present invention.

The nucleic acid complex of the present invention can be characterized by a variety of methods as known in the art. For example, the formation of the nucleic acid complex can be measured by Zeta potentials, dynamic light scattering, and visualized by AFM images. For example, dynamic light scattering of a nucleic acid complex can reveal the average size of the nucleic acid complex.

It is an important aspect of the present invention that the nucleic acid complex can be used for delivery of a nucleic acid to a cell. In some embodiments, the cell is a cancer cell.

In some embodiments, the method comprises the step of bringing a nucleic acid complex comprising a nucleic acid into contact with the cell, wherein the nucleic acid complex comprises the nucleic acid, a macrocyclic compound, and a pendant polymer, wherein the pendant polymer is modified with a hydrophobic group, and wherein the macrocyclic compound and the pendant polymer form a host:guest polymer complex. In some embodiments, the nucleic acid is siRNA or pDNA. In some embodiments, the nucleic acid is siRNA. In other embodiments, the nucleic acid is pDNA. In some embodiments, the hydrophobic group is a lipid.

In some embodiments, the macrocyclic compound is a modified cyclodextrin. In other embodiments, the modified cyclodextrin is a modified β-cyclodextrin comprising an amino moiety. In certain embodiments, the macrocyclic compound is mono-6-(amino)-6-deoxy-β-cyclodextrin, mono-6-(N,N'-dimethylethane-1,2-diamine)-6-deoxy-β-cyclodextrin, or mono-6-(N'-(2-aminoethyl)ethane-1,2-diamine)-6-deoxy-β-cyclodextrin, hepta-6-(2'-aminoethyl)amino-β-cyclodextrin, hepta-6-(2'-hydroxyethylamino)-β-cyclodextrin, or hepta-6-(hydrazino)-β-cyclodextrin.

In some embodiments, the pendant polymer comprises a poly(vinyl alcohol), polysaccharide, polyester, or polyamide backbone.

In some embodiments, the pendant polymer comprises a poly(vinyl alcohol) backbone.

In some embodiments, the pendant polymer comprises a poly(ethylene glycol) pendant group.

In some embodiments, the hydrophobic group is cholesterol, or a derivative or analog thereof, and the cholesterol, or a derivative or analog thereof, is linked through an acetal linkage to the backbone of the pendant polymer.

In some embodiments, the host:guest polymer complex condenses the nucleic acid to form a nanoparticle in a size of from about 120 nm to about 170 nm.

In some embodiments, the cell is in vitro or in vivo. In some embodiments, the cell is in vitro. In other embodiments, the cell is in vivo.

In some embodiments, the cell is a cancer cell.

In some embodiments, the method for bringing the nucleic acid complex, or a pharmaceutical composition comprising the same, into contact with a cell is not limited, as long as a suitable amount of the nucleic acid complex is brought into contact with the cell into which the nucleic acid is to be introduced. In some embodiments, the contact can be carried out in the presence of blood serum. In some embodiments, the contact can be carried out by direct injection into a tissue; intravenous, subcutaneous, intramuscular, intraperitoneal, or intraocular injection, or injection into the digestive tract, a tooth, or the like.

In some embodiments, the cell into which a nucleic acid is delivered can be a cultured cell, a cell isolated from an organism (including established cell lines), a cell in vivo, and may be derived from a human or a non-human animal. The nucleic acid complex can be applied either in vitro or in vivo.

When the nucleic acid is siRNA, the corresponding siRNA complex showed a gene knockdown efficiency of about 65% or above. In some embodiments, the gene knockdown efficiency is from about 50% to about 95%. In other embodiments, the gene knockdown efficiency is from about 60% to about 95%. In some embodiments, the gene knockdown efficiency is from about 65% to 95%. In other embodiments, the gene knockdown efficiency is from about 65% to about 85%. In certain embodiments, the gene knockdown efficiency is from about 70% to about 85%. In some embodiments, the gene knockdown efficiency is about 95% or higher.

The nucleic acid complex of the invention offers a low toxicity and high efficiency system for delivering a nucleic acid to a cell based on self-assembly of a macrocyclic compound with a hydrophobically-modified pendant polymer. The backbone of the pendant polymer, linked to the hydrophobic group via a pH-sensitive acetal linkage, provides a scaffold for binding of the macrocyclic molecule that is capable of condensing the nucleic acid into nanoparticles. The hydrophobic group is capable of degrading within acidic endosomes to effect the release of the nucleic acid from the nucleic acid complex through breakage of the acetal linkage. The nucleic acid complex of the present invention is nearly 3-4 orders of magnitude less cytotoxic than conventional cationic polymer transfection agent, for example, polyethylene imine (PEI) which is widely investigated as a gene carrier. Further, the nucleic acid complex of the present invention is capable of achieving transfections efficiencies that are comparable and superior to those of 25 kD bPEI. When the nucleic acid is siRNA, the siRNA complex of the present invention can safely and effectively deliver the siRNA into a cell and the siRNA can be freed inside of endosomes under its acidic environment, thus efficiently silencing disease-related genes.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specification and which are not in the prior art.

The invention will be further illustrated with reference to the following illustrative examples, which are not intended to limit the scope of the invention in any manner.

EXAMPLES

Materials and Methods

All solvents were of reagent grade, purchased from commercial sources, and used without further purification, except DMF and toluene, which were dried over $CaH_2$ under $N_2$, filtered and distilled under reduced pressure. β-CD, cholesteryl chloroformate, bromopropylamine hydrobromide, 4-hydroxybenzaldehyde, $Na_2CO_3$, 1,1-carbonyldiimidazole (CDI), and p-toluenesulfonyl acid (pTSA) and p-toluenesulfonyl chloride were obtained from Sigma-Aldrich. Qiagen kits were purchased from Qiagen. $^1H$ NMR spectra were recorded on a 300 MHz VARIAN INOVA 300 NMR spectrometer at 30° C. Chemical shifts were referenced to the residual protonated solvent peak.

Anti-GFP siRNA and Allstars negative control siRNA were procured from Qiagen and the CHO-GFP cells were provided by Prof. Z. R. Lu from Case Western University.

Dynamic Light Scattering and Atomic Force Microscopy

The sizes, size distributions and zeta potentials of the materials were evaluated by dynamic light scattering using a particle size analyzer (Zetasizer Nano S, Malvern Instruments Ltd.) at 20° C. with a scattering angle of 90°. AFM imaging of the nanoparticles was conducted in tapping mode (Multi-Mode, Veeco, USA) using dry samples on mica. The AFM tips (PPP-NCH, Nanoscience Instruments, Inc., USA) had a typical radius of 7 nm or less, and the images were recorded with a scan rate of 0.5 or 1 Hz. Samples were prepared by dropping 2 mL of solution on a mica surface, followed by overnight drying at 20° C.

Cell Viability Assay (1)

The cytotoxicity of the amino-CD derivatives in comparison with bPEI (25 kDa) was evaluated using the MTS assay in CHO-GFP cell lines. The relative cell viabilities were measured as a function of amine densities of the polymers. The cells were cultured in complete F12 medium supplemented with 10% FBS at 37° C., 5% $CO_2$, and 95% relative humidity. The cells were seeded in a 96-well microtiter plate (Nunc, Wiesbaden, Germany) at densities of 10,000 cells/wells. After 24 h, culture media were replaced with serum-free culture media containing increasing amine concentrations of amino-CD, polymer and the polymer:CD complexes and the cells were incubated for 24 h. After 24 h, 15 μL of MTS reagent was added to each well and incubated for 2 h. Following the incubation period, the absorbance was measured using a microplate reader (Spectra Plus, TECAN) at a wavelength of 492 nm. The relative cell viability (%) related to control cells cultured in media without polymers was calculated with $[A]_{test}/[A]_{control} \times 100\%$, where $[A]_{test}$ is the absorbance of the wells with polymers and $[A]_{control}$ is the absorbance of the control wells. All experiments were conducted for three samples and averaged. The median lethal dose ($LD_{50}$) is the dose of a toxic material that kills half (50%) of the cells tested. In this study, $LD_{50}$ was the concentration of a gene carrier at which the relative cell viability decreased to 50%.

Cell Viability Assay (2)

The cytotoxicity of the amino-β-$CD^+$ complexes relative to bPEI (25 kDa) was evaluated using the MTT assay in HeLa cells. The cells were cultured in DMEM medium supplemented with 10% FBS at 37° C., 5% $CO_2$, and 95% relative humidity. The cells were seeded in 96-well microtiter plates (Nunc, Wiesbaden, Germany) at densities of 10,000 cells/well. After 24 h, the culture medium was replaced with serum-supplemented culture medium containing serial dilutions of amino-β-$CD^+$, and the cells incubated for an additional 24 h. Then, 10 μL of sterile-filtered MTT stock solution in PBS (5 mg/mL) was added to the wells, reaching a final MTT concentration of 0.5 mg/mL. After 5 h, unreacted dye was removed by aspiration. The formazan crystals were dissolved in DMSO (100 μL/well), and the absorbance at 570 nm measured using a microplate reader (Spectra Plus, TECAN). The percent cell viability, compared to control cells cultured in media without polymers, was calculated as $[A]_{test}/[A]_{control} \times 100\%$, where $[A]_{test}$ is the absorbance of the wells with polymers and $[A]_{control}$ is the absorbance of the control wells. Experiments were conducted in triplicate and averaged. The median lethal dose ($LD_{50}$) is the dose of a toxic material that kills half (50%) of the cells tested. In this study, $LD_{50}$ was taken as the concentration of a gene carrier causing a relative cell viability decrease to 50%.

In Vitro Gene Knockdown Experiment

CHO-GFP cells were cultured in complete F12 medium supplemented with 10% FBS at 37° C., 5% $CO_2$, and 95% relative humidity. 150,000 cells/well were seeded in a 24 well plate. After 48 h, the culture media was replaced with serum-supplemented media containing the siRNA complexes. The cells were incubated with the complexes for 4 h, after which the spent media was aspirated and fresh serum-supplemented media was added. After 24 h incubation, the media was aspirated and the cells were washed with PBS, trypsinized and analyzed by FACS using the FL1 channel. The percentages of cells displaying GFP fluorescence were calculated with respect to the number of cells showing a loss in fluorescence relative to the untreated samples.

Gel Shift Assay

The complexation ability of the systems was studied by gel shift assay. Agarose gels (1% w/v) containing ethidium bromide were made in 1×TE buffer. Transfection complexes were loaded onto the gel at various N:P ratios and 200 ng of DNA added to the wells. The gels were run at 50V for about 1 h and visualized.

In Vitro Transfection of mhGFP pDNA

HeLa cells were cultured in DMEM medium supplemented with 10% FBS at 37° C., 5% $CO_2$, and 95% relative humidity. Cells were seeded in 24 well plates at a density of 100,000 cells/well. After 48 h, the culture media was replaced with media (serum-free or 10% serum-supplemented) containing the transfection complexes prepared at a 20:1 N:P ratio using mhGFP pDNA. The cells were incubated with the transfection complexes for 24 h, after which the spent media was aspirated and fresh serum-supplemented media was added. After incubation for 24 h, the media was aspirated and the cells washed with PBS, trypsinized and analyzed by FACS using excitation and emission filters of 488 nm and 530 nm, respectively.

Example 1

Synthesis of mono-6-(p-toluenesulfonyl)-6-deoxy-β-cyclodextrin (β-CD-OTs)

β-Cyclodextrin (35.0 g, 30.8 mmol) was dissolved in 350 mL $H_2O$ with 1-(p-toluenesulfonyl)imidazole (8.9 g, 40.0 mmol) and stirred at 20° C. for 4 h. NaOH (50 mL, 20% w/v) was then added to the mixture and stirred for 10 min, inducing a precipitate. The precipitate was filtered off and the filtrate was collected, then neutralized to pH 7 with ~25 g $NH_4Cl$ to form another precipitate. This precipitate was collected by filtration and washed with 100 mL of $H_2O$ three times and 100 mL of acetone twice and dried overnight under vacuum. Since both mono- and ditosylate forms existed along with unreacted β-CD, an HP20 (C18) column was run. The mixture was loaded in bulk water and eluted with water until no more β-CD-OH emerged, at which point methanol was used as eluent and fractions were collected. Fractions were confirmed via TLC using isopropanol:$H_2O$:EtOAc:30% $NH_4OH$ (3:2:1:1) as solvent and acid stain (20% $H_2SO_4$) visualization. Yield: 12.3 g (35.1%). $^1H$ NMR (300 MHz, DMSO-$D_6$, δ): 7.80-7.66 (d, 2H, S-Benzene), 7.50-7.33 (d, 2H, Benz-$CH_3$), 5.93-5.48 (b, 14H, OH on C2, C3 of CD), 4.87-4.70 (s, 7H, C1H of CD), 4.63-4.08 (b, 6H, OH on C6 of CD), 3.75-3.43 (m, 28H, C2H, C3H, C4H, and C5H of CD, overlap with HDO), 3.43-3.11 (m, 14H, C6H of CD), 2.43-2.34 (s, 3H, $CH_3$ on OTs).

Example 2

Synthesis of mono-6-azido-6-deoxy-β-cyclodextrin (β-CD-$N_3$)

β-CD-OTs (5.326 g, 4.131 mmol) was dissolved in 500 mL $H_2O$ with $NaN_3$ (7.5 g, 115.367 mmol) and stirred at reflux overnight. The mixture was then cooled to 20° C. and filtered, with the filtrate being concentrated down to at least 5% of the original volume. Trichloroethylene (20 mL) was then added dropwise and the solution was stirred for 30 min at 20° C. The resulting biphasic mixture was then centrifuged at 4000 rpm for 12 minutes at 15° C. The bottom phase and intermediate white solid were collected and trichloroethylene was removed under reduced pressure and the solid dried further under vacuum. Impure yield=4.3 g (89.7%). The crude sample was taken to next step for reduction without further purification.

Example 3

Synthesis of mono-6-amino-6-deoxy-β-cyclodextrin (1)

β-CD-$N_3$ (4.565 g, 3.935 mmol) was dissolved in 30 mL DMF with $Ph_3P$ (1.5 g, 5.7 mmol) and stirred at 20° C. for 3 h. $NH_4OH$ (20 mL, 30% v/v) was then added and stirred overnight. The mixture was then precipitated in 400 mL acetone and dried under vacuum to give a crude solid product. Yield=3.2 g (71.7%). The crude product was then dissolved in 100 mL $H_2O$ and the undissolved β-CD-$N_3$ was filtered off. This solution was then loaded onto an IEX column (BioRex 70, 100-200 mesh, $NH_4^+$ form, partially pressure packed in an empty SNAP 100 g cartridge) and run on a Biotage SP40 system at 15 mL/min 500 mL (3.7 CV) $H_2O$ was eluted to remove any unreacted OTs and $N_3$, followed by 1 CV 0.1 M $NH_4OH$, 1 CV 0.5 M $NH_4OH$, and 5 CV 1M $NH_4OH$ to remove the β-CD-$NH_2$. Fractions were checked via 80:20 MeOH:$H_2O$ TLC with anisaldehyde staining. The appropriate fractions were combined and concentrated by rotary evaporation to give pure product. Yield=1.429 g (32.0%). $^1H$ NMR (300 MHz, $D_2O$, δ): 5.04-4.88 (s, 7H, C1H of CD), 3.94-3.66 (m, 28H, C2H, C3H, C4H, and C5H of CD), 3.63-3.32 (m, 14H, C6H of CD), 3.13-3.05 (d, 1H, $NH_2$), 2.90-2.79 (b, 1H, $NH_2$).

Example 4

Synthesis of Mono-6-(N,N'-dimethylethane-1,2-diamine)-6-deoxy-1'-cyclodextrin (2)

β-CD-OTs (500.0 mg, 0.388 mmol) was dissolved in 5 mL dry DMF with 100 mg NaI. N,N'-Dimethylethane-1,2-diamine (1.28 mL, 11.72 mmol) was then added under $N_2$ and the reaction mixture was stirred overnight at 70° C. under $N_2$. The next day the reaction mixture was cooled and precipitated in 50 mL acetone, giving a white precipitate. Unreacted tosylate was removed via the same ion-exchange methods as described above for β-CD-$NH_2$. Yield=374 mg (80.0%). $^1H$ NMR (300 MHz, $D_2O$, δ): 5.02-4.87 (s, 7H, C1H of CD), 3.93-3.64 (m, 29H, C2H, C3H, C4H, and C5H of CD and NH), 3.61-3.29 (m, 14H, C6H of CD), 3.01-2.36 (m, 10H, $N^1$—$CH_2$, $N^2$—$CH_2$, and $N^2$—$(CH_3)_2$).

Example 5

Synthesis of Mono-6-(N'-(2-aminoethyl)ethane-1,2-diamine)-6-deoxy-1'-cyclodextrin (3)

This compound was prepared in the same manner as Compound 2, except that N'-(2-aminoethyl)ethane-1,2-diamine was used as the nucleophile instead of N,N'-dimethylethane-1,2-diamine Yield=408 mg (86.3%). $^1H$ NMR (300 MHz, $D_2O$, δ): 5.02-4.89 (s, 7H, C1H of CD), 3.89-3.69 (m, 30H, C2H, C3H, C4H, and C5H of CD, N1H, and N2H), 3.58-3.40 (m, 16H, C6H of CD, $N^1$—$CH_2$), 3.58-3.40 (m, 4H, $N^2$—$CH_2$, $NH_2$—$CH_2$), 3.13-3.05 (m, 2H, $N^2$—$CH_2$), 2.99-2.62 (b, 2H, $NH_2$).

Example 6

Synthesis of cholesteryl-(3-bromopropyl)carbamate (Chol-BPA)

Cholesteryl chloroformate (1.63 g, 3.63 mmol) was dissolved in 10 mL dry DCM with 1.68 mL N,N-diisopropylethylamine (9.65 mmol) followed by the addition of bromopropylamine-HBr (0.5 g, 3.6 mmol) under $N_2$. The reaction mixture was stirred under $N_2$ overnight at 20° C., and then washed three times with water and dried over $Na_2SO_4$. The product solution was then loaded on a Biotage SP40 system (M40 Si column, 20 mL/min, 20 mL DCM loading ~2 g) and eluted with 6 CV of 99:1 DCM:$Et_2O$. Yield: 1.126 g (56.8%). $^1H$ NMR (300 MHz, $CDCl_3$, δ): 5.41-5.32 (s, 1H, Vinyl-H), 4.82-4.67 (b, 1H, NHCOO—CH), 4.60-4.43 (b, 1H, NH), 3.50-3.38 (t, 2H, Br—$CH_2$), 3.37-3.26 (q, 2H, $CH_2$—NHCOO), 2.440-0.78 (m, 42H, cholesteryl), 0.69-0.63 (s, 3H, —$CH_3$).

Example 7

Synthesis of Chol-Ph-CHO

Chol-BPA (1.126 g, 2.045 mmol) was dissolved in bulk acetone with 4-hydroxybenzaldehyde (250 mg, 2.047 mmol) and $K_2CO_3$ (0.707 mg, 5.115 mmol) and then heated at reflux overnight. The acetone was removed and replaced with ~20 mL DCM, and the solution was washed with $H_2O$ three times and dried over $Na_2SO_4$. The product solution was then loaded on the same Biotage system (M40 Si column, 35 mL DCM loading ~1 g) and eluted with 4.1 CV of 99:1 DCM:$Et_2O$ at 10 mL/min, 3 CV at 15 mL/min, 2 CV at 20 mL/min, and 1 CV of 40:60 DCM:Ether at 40 mL/min Yield: 310 mg (25.6%). $^1H$ NMR (300 MHz, $CDCl_3$, δ): 9.95-9.84 (s, 1H, CHO), 7.92-7.76 (d, 2H, CHO-Benz), 7.08-6.93 (d, 2H, $OCH_2$-Benz), 5.41-5.32 (s, 1H, Vinyl-H), 4.90-4.75 (b, 1H, NHCOO—CH), 4.59-4.39 (b, 1H, NH), 4.19-4.03 (t, 2H, BenzO-$CH_2$), 3.48-3.30 (b, 2H, $CH_2$—NHCOO), 2.38-0.79 (m, 42H, cholesteryl), 0.71-0.61 (s, 3H, —$CH_3$).

Example 8

Synthesis of Chol-PVA

Poly(vinyl alcohol) (MW=27 kDa) (243.0 mg, 0.009 mmol) was dissolved in 15 mL DMSO at 75° C., followed by the addition of Chol-HB (800.0 mg, 1.35 mmol) and pTSA (100 mg, 0.580 mmol). The solution was stirred for 2 d at 75° C., then cooled to room temperature and precipitated in acetone to give a crude white solid. Yield: ~1 g. Due to the poor solubility of this intermediate, the crude product was taken directly to the next step without further purification or characterization.

Example 9

Synthesis of Chol-PVA-PEG

PVA-Chol (250 mg, 0.0034 mmol) was dissolved in 15 mL DMSO with carbonyldiimidazole (47.2 mg, 0.29 mmol) under $N_2$ for 1 d followed by the addition of $H_2N$-PEG2000-OMe (1.2 g, 0.60 mmol) under $N_2$ for an additional day. The crude mixture was then loaded into a dialysis bag (Fisher-Brand, 6000-8000 MWCO) and dialyzed against DMSO and $H_2O$ for 2 d each followed by lyophilization. Yield over two steps: 429.91 mg, (47.0%). Pendant groups: Chol-HB: ~15.17H (PVA) per unit, ~80.82 units, ~13.2% of PVA-OH (loading); PEG2000-OMe: ~7.45H (PVA) per unit, ~164.56 units, ~26.9% of PVA-OH (loading). Approximate MW by NMR: ~406.53 kDa. $^1$H NMR (300 MHz, DMSO-$D_6$, δ): 7.72-7.44 (m, aromatic of Chol-HB), 6.00-5.90 (t, CH of acetal), 4.70-4.61 (s, NH of PEG), 4.49-4.39 (s, NH of Chol-HB), 4.23-4.15 (s, Ar—O—CH2), 3.95-3.67 (b, OH of PVA), 3.59-3.05 (m, PEG $CH_2$ and $CH_3$), 1.97-0.58 (m, residual cholesteryl, overlap with PVA), 1.78-1.11 (b, PVA CH and $CH_2$, overlap with residual cholesteryl).

Example 10

Evaluation of Non-Covalent Pendant Polymer Assemblies to Condense siRNA

Two different complexation methods (Scheme 1) were used to evaluate the relative capacity of Chol-PVA-PEG:amino-β-CDs guest:host polymer assemblies toward siRNA condensation.

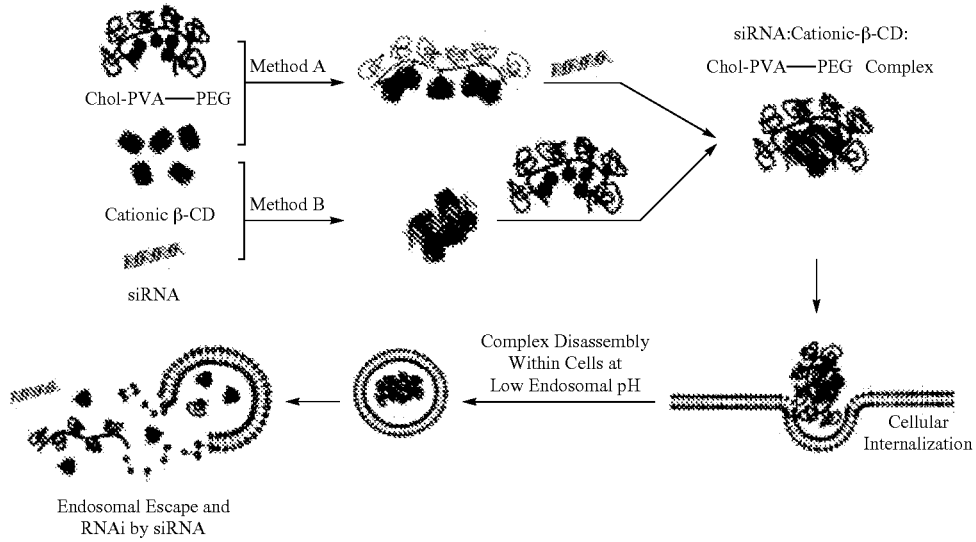

Figure 9:
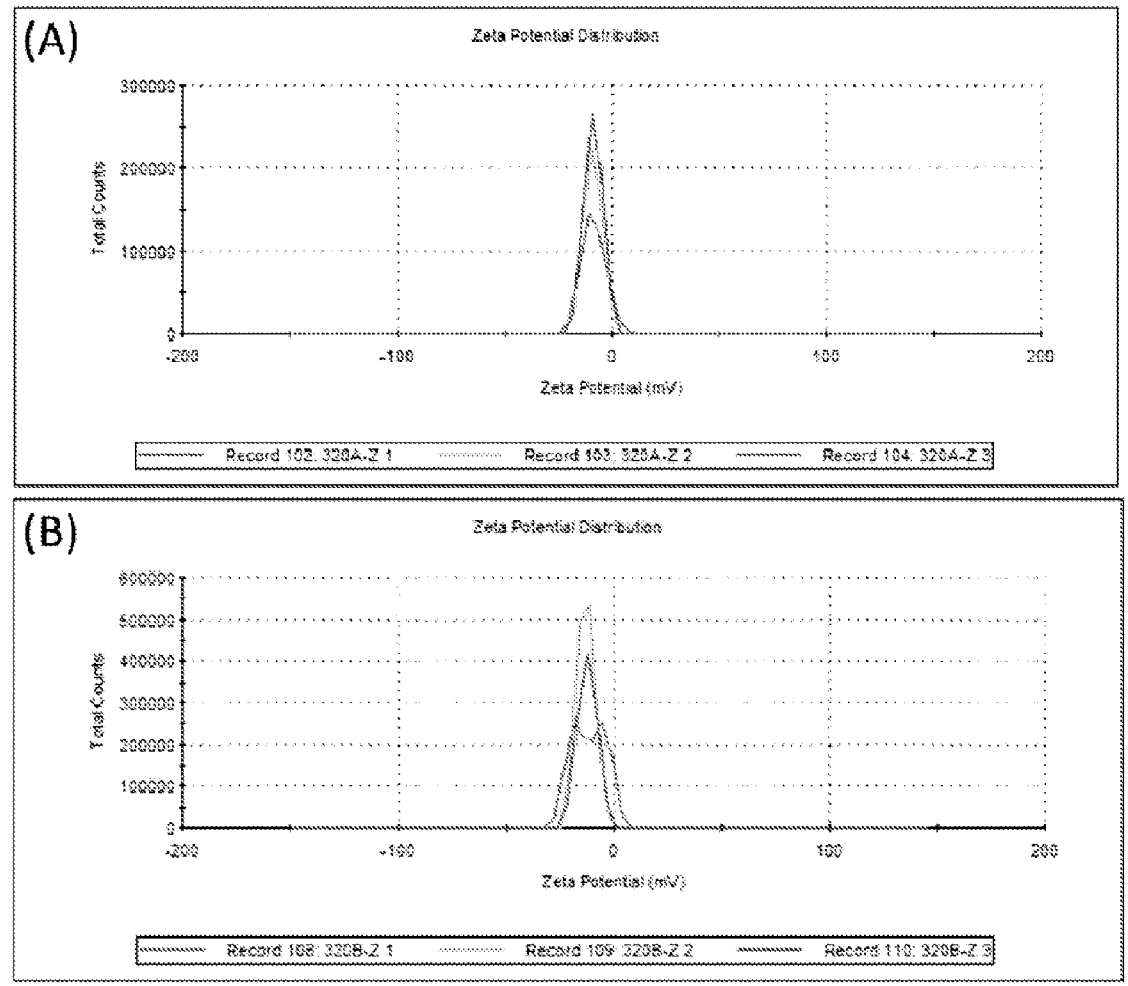
FIG. 9 depicts Zeta Potential Measurements of Chol-PVA-PEG:3:siRNA complexes at N/P=20 formulated by (A) Method A and (B) Method B.

Scheme 1: Conceptual diagram of Chol-PVA—PEG:amino-β-CD:siRNA complexation and endosomal escape In Method A, Chol-PVA-PEG was pre-associated with amino-β-CDs before addition to the siRNA solution. In Method B, the siRNA was first complexed with amino-β-CDs, followed by addition of Chol-PVA-PEG. Zeta potentials were measured for both types of complexes to determine the surface charge of the resulting transfection particles (Table 1 and FIG. 9). This data showed that complexes formed by both methods, had slightly negative zeta potentials (ζ<−8 mV). As the N/P ratio increases from 10 to 20, the ζ-potential approaches neutral. Method B (ζ −16 mV--12 mV) particles were shown to be more negatively charged than those produced by Method A (ζ −10 mV--8 mV). Amongst the CD variants, particles formulated from 1 had the lowest observed ζ, followed by 2 and 3, respectively. The absence of a positive charge on the surface could be due to the high loading of PEG on the polymer backbone, which is able to effectively shield the positive charges arising from the cationic CDs. These results are encouraging since a positive surface charge is considered to be one of the major reasons for nanoparticle opsonization or macrophage uptake (Shan, et al. *Coll. Surfaces B: Bioint,* 2009, 72, 303). Gabizon and Papahadjopoulos have previously shown that liposomes with a slight negative charge have prolonged circulation times and enhanced tumor uptake due to RES evasion (Gabizon, et al. *Proc. Natl. Acad. Sci. USA,* 1988, 85, 6949).

TABLE 1

Zeta Potential Measurements of Chol-PVA-PEG:Amino-β-CD:siRNA complexes

| Amino-β-CD | Method of Formulation | N/P = 10 | | N/P = 20 | |
|---|---|---|---|---|---|
| | | ζ (mV) | Std. Error | ζ (mV) | Std. Error |
| 1 | A | −12.6 | 0.551 | −10.2 | 0.153 |
| | B | −19.9 | 1.53 | −16.8 | 0.9 |
| 2 | A | −13.9 | 1.14 | −11.2 | 0.981 |
| | B | −13.3 | 4.71 | −15.4 | 0.755 |
| 3 | A | −11.0 | 0.451 | −8.6 | 0.272 |
| | B | −14.3 | 1 | −12.5 | 0.7 |

Figure 10:
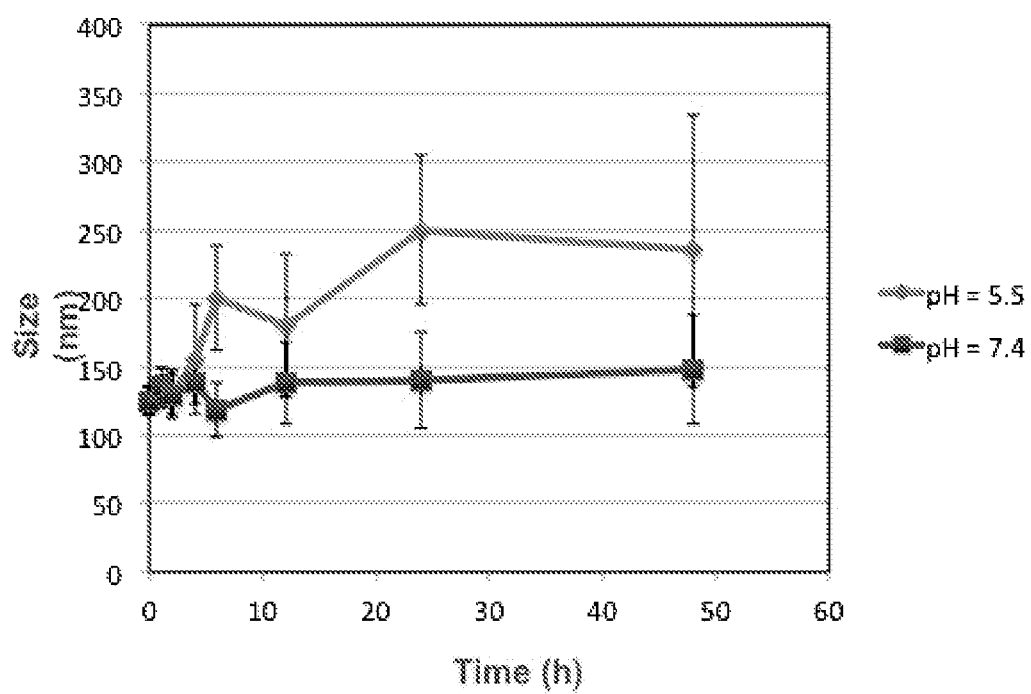
FIG. 10 depicts DLS Measurements of Chol-PVA-PEG:3: siRNA at pH 5.5 and pH 7.4 as a function of time. The particle size increases significantly with time at pH 5.5, and after 4 h, multiple particle populations are seen. This can be contributed to hydrolysis of the polymer acetal linkages over time. Complexes are relatively stable at pH 7.4 up to 24 h, with a slight increase in PDI noted at 48 h.
Figure 11:
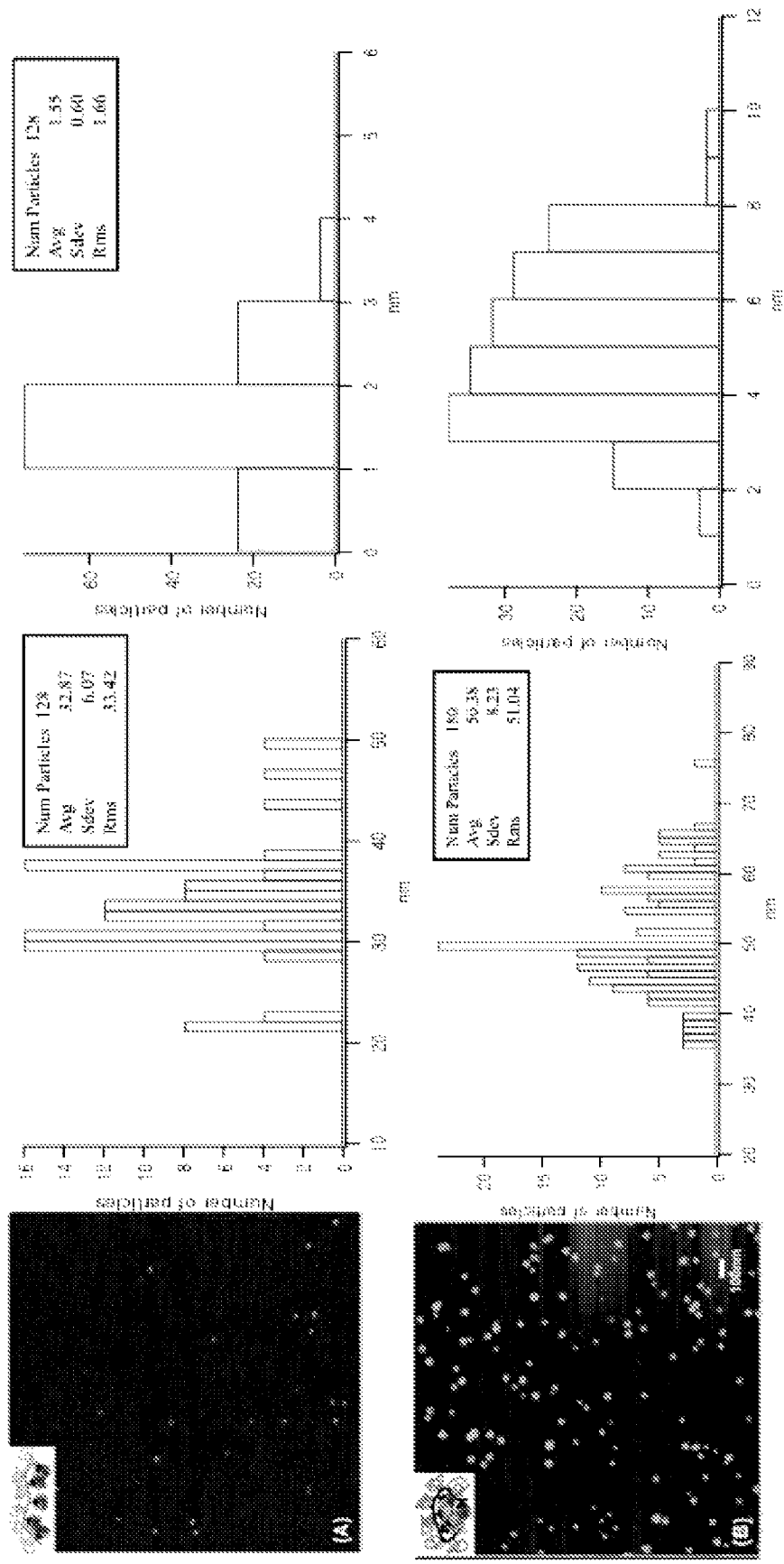
FIG. 11 depicts size distributions of (A) Chol-PVA-PEG:3 and (B) Chol-PVA-PEG:3:siRNA at N/P=10.
Figure 12:
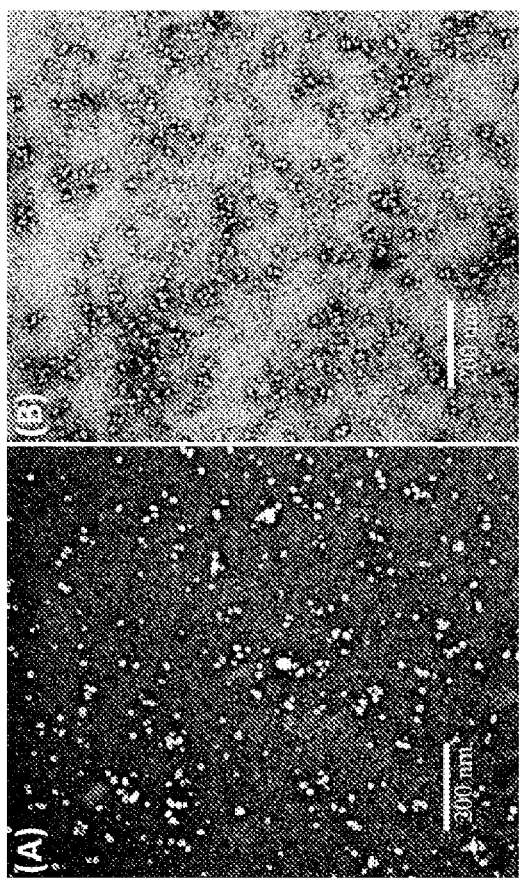
FIG. 12 depicts TEM images of (A) Chol-PVA-PEG:1 and (B) Chol-PVA-PEG:1:siRNA at N/P=5 prepared by Method A.
Figure 13:
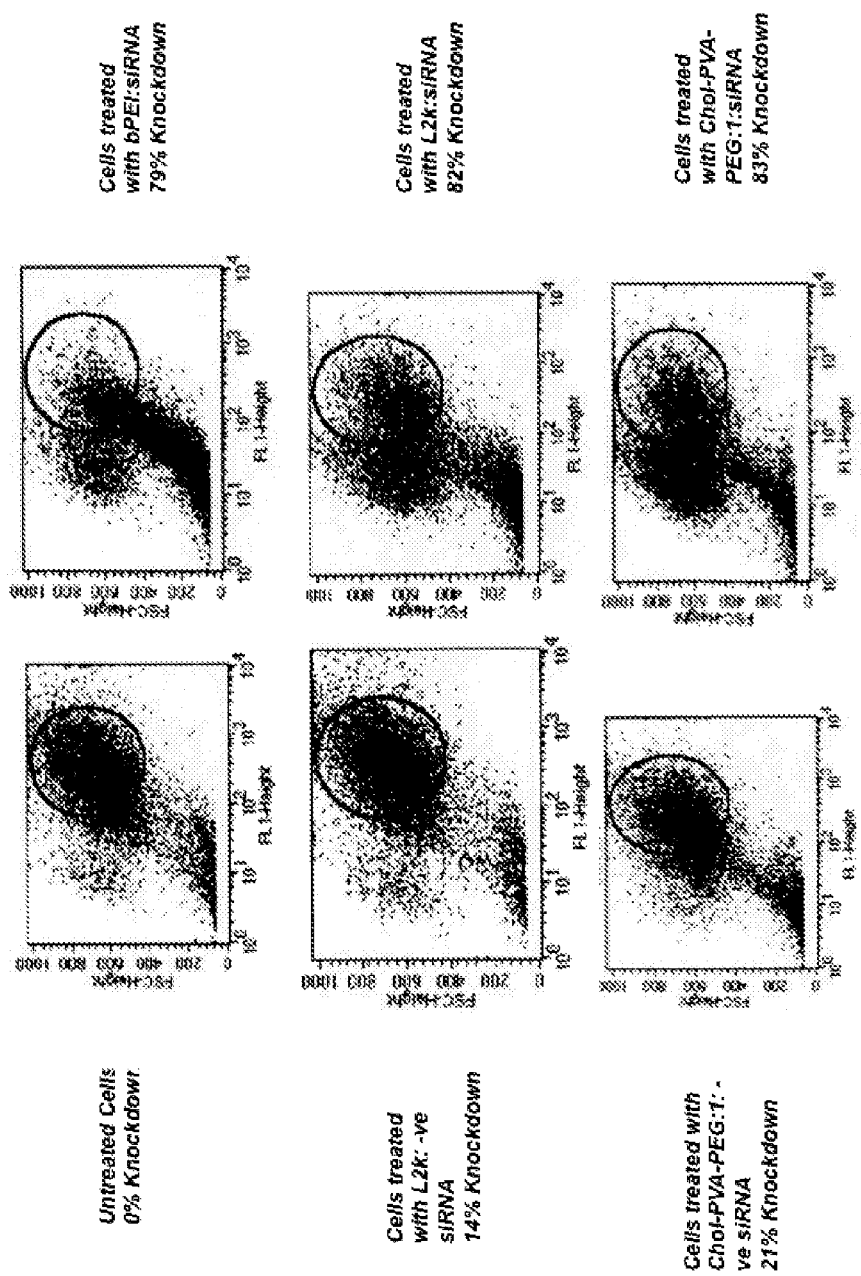
FIG. 13 depicts a flow cytometric analysis of gene silencing of CHO-GFP cells with 100 nM of anti-GFP siRNA in each well. Comparison of complex of siRNA:3:Chol-PVA-PEG relative to siRNA:bPEI (25K) and siRNA:L2k at N/P ratio=20 in serum-supplemented media in CHO-GFP cells.

Dynamic light scattering (DLS) showed that the complex sizes produced by these different materials and methods were in the size range, 120 nm-170 nm, with higher N/P ratios producing smaller particles (Table 2 and FIG. 10). In general, the method of formulation did not significantly affect the size of the particles. Compound 3 was able to generate smaller particles than 2, which formed particles smaller than 1, suggesting that an increase in CD charge leads to smaller particle formation.

TABLE 2

DLS Measurements of Chol-PVA-PEG:Amino-β-CD:siRNA

| Amino-β-CD | Method of Formulation | N/P = 10 | | N/P = 20 | |
|---|---|---|---|---|---|
| | | Size (nm) | PDI | Size (nm) | PDI |
| 1 | A | 162.5 | 0.348 | 133.9 | 0.332 |
| | B | 151.2 | 0.243 | 139.8 | 0.346 |
| 2 | A | 153.9 | 0.382 | 128.1 | 0.392 |
| | B | 141.7 | 0.335 | 123.9 | 0.369 |
| 3 | A | 137.8 | 0.421 | 125.8 | 0.331 |
| | B | 139.9 | 0.359 | 125.9 | 0.346 |

Example 11

AFM Images of Chol-PVA-PEG:amino-β-CD

Figure 2:
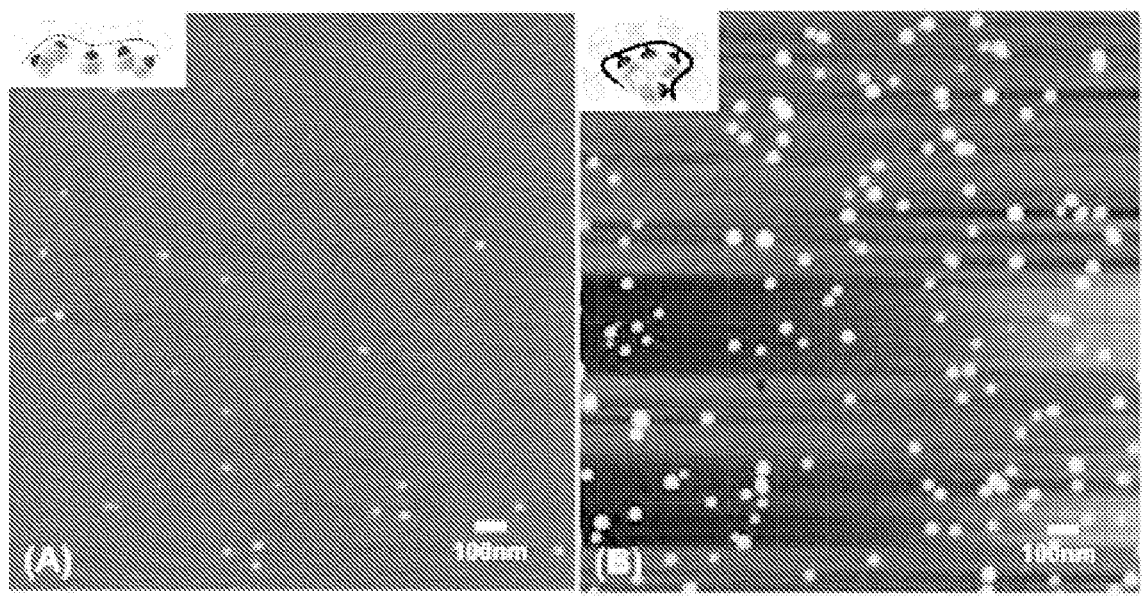
FIG. 2 depicts AFM images of (A) Chol-PVA-PEG:3 and (B) Chol-PVA-PEG:3:siRNA at N/P=10 (insets showing structures within AFM images). Scale bar=100 nm.

AFM images of Chol-PVA-PEG:amino-β-CD samples revealed the presence of spherical particles (FIG. 2A) of average diameters <30 nm and heights of 1.5 nm. Upon addition of siRNA at N/P=10, uniform spherical particles were formed that were of an average diameter of 60 nm and height of 5 nm (FIG. 2B). The low heights may be due to to deformation of the particles during the sample preparation for AFM. The sizes determined by AFM are smaller than those measured by DLS due to the dry nature of the AFM samples (i.e., polymer solvent-swelling is absent). These results support the conclusion that supramolecular complexation of Chol-PVA-PEG with amino-β-CD produces a non-covalent assembly that is capable of condensing siRNA into compact and uniform spherical particles.

Example 12

Figure 3:
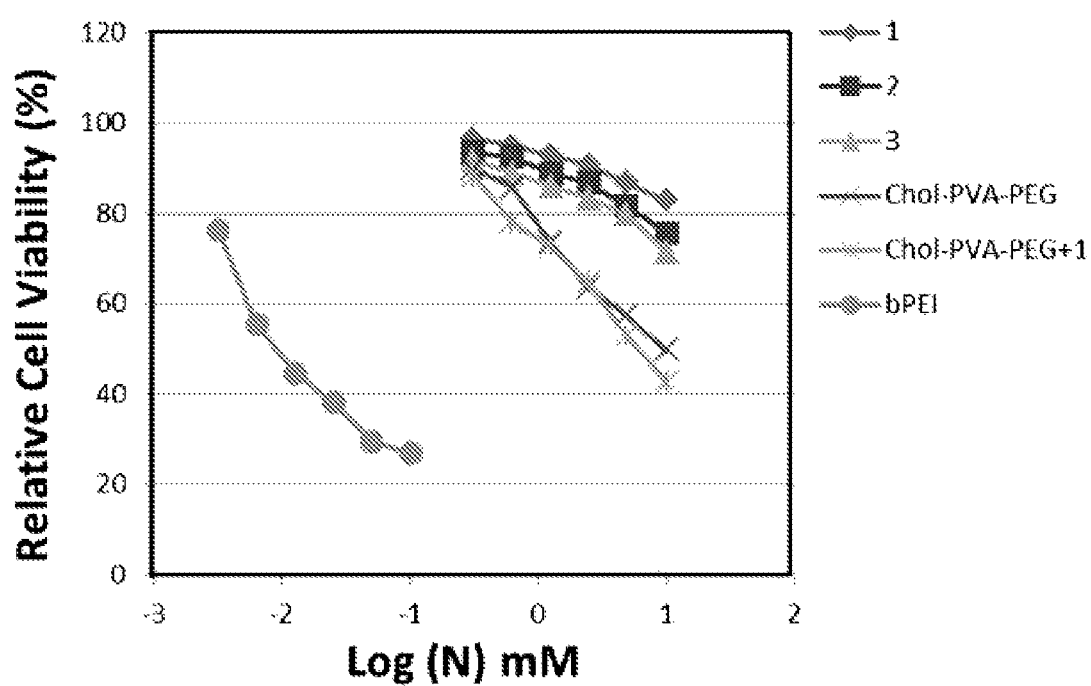
FIG. 3 depicts cell viabilities of 1, 2, 3, Chol-PVA-PEG and Chol-PVA-PEG+1 host:guest pendant polymer complexes in CHO-GFP cells using 25 kD bPEI as control. The cells were treated with increasing concentrations of amino-β-CDs, Chol-PVA-PEG, Chol-PVA-PEG+1 and bPEI for 24 h in serum-free media before analysis by MTS assay.

In-Vitro Cytotoxicity of Amino-β-CD, Chol-PVA-PEG, and their Host:Guest Complexes The in vitro cytotoxicity of amino-β-CDs, Chol-PVA-PEG, and their host:guest complexes are a factor for their consideration as a safe non-viral vector. FIG. 3 shows that Chol-PVA-PEG, the amino-β-CDs, and the Chol-PVA-PEG:1 host:guest complex were nearly 3-4 orders of magnitude less cytotoxic than bPEI, (i.e., the LD50's of bPEI, Chol-PVA-PEG and 1:1 Chol-PVA-PEG:1 were 0.01 mM, 9.5 mM and 7.9 mM respectively, while those of 1, 2, and 3 were >10 mM and had negligible effect on the cell viability).

Example 13

In Vitro Gene Knockdown Efficiency

Figure 4:
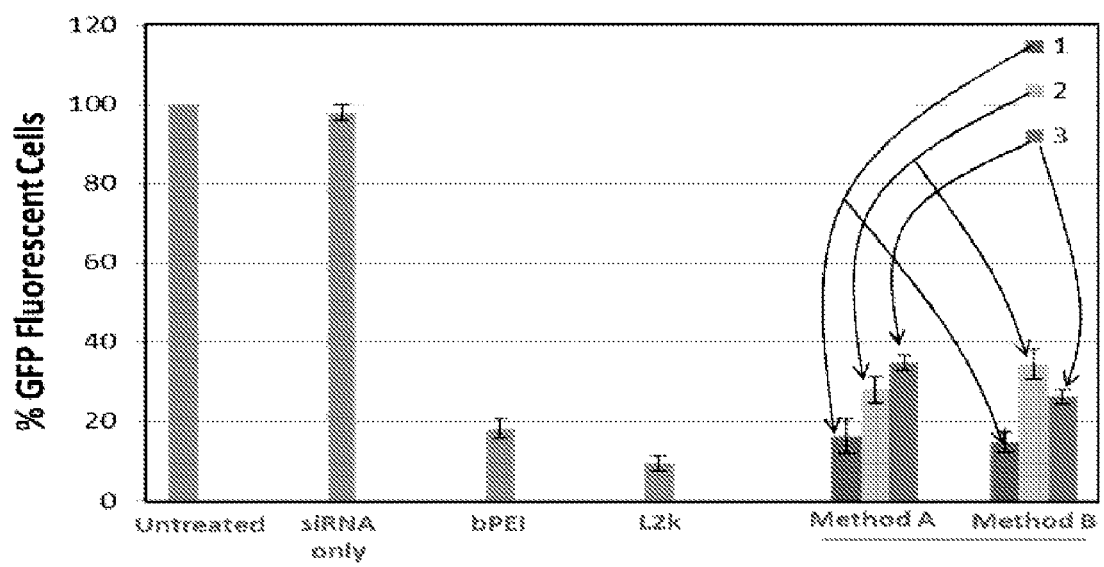
FIG. 4 depicts in vitro GFP knockdown efficiencies of amino-β-CD host:guest complexes with Chol-PVA-PEG and anti-GFP siRNA in CHO-GFP cells (in presence of serum) with 25 kD bPEI and Lipofectamine 2000 (L2k) as controls. 100 nM of anti-GFP siRNA/well.
Figure 5:
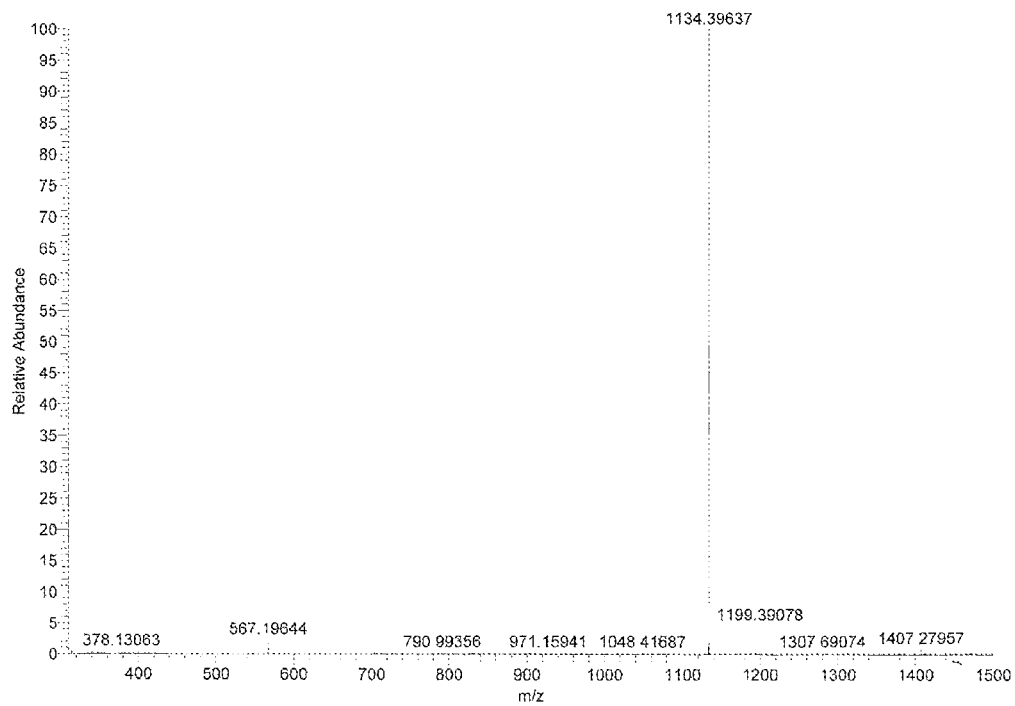
FIG. 5 depicts a high resolution Mass Spectrum of amino-β-cyclodextrin 1. Theoretical Mass: 1133.38575. Experimental Mass: 1133.39637.
Figure 6:
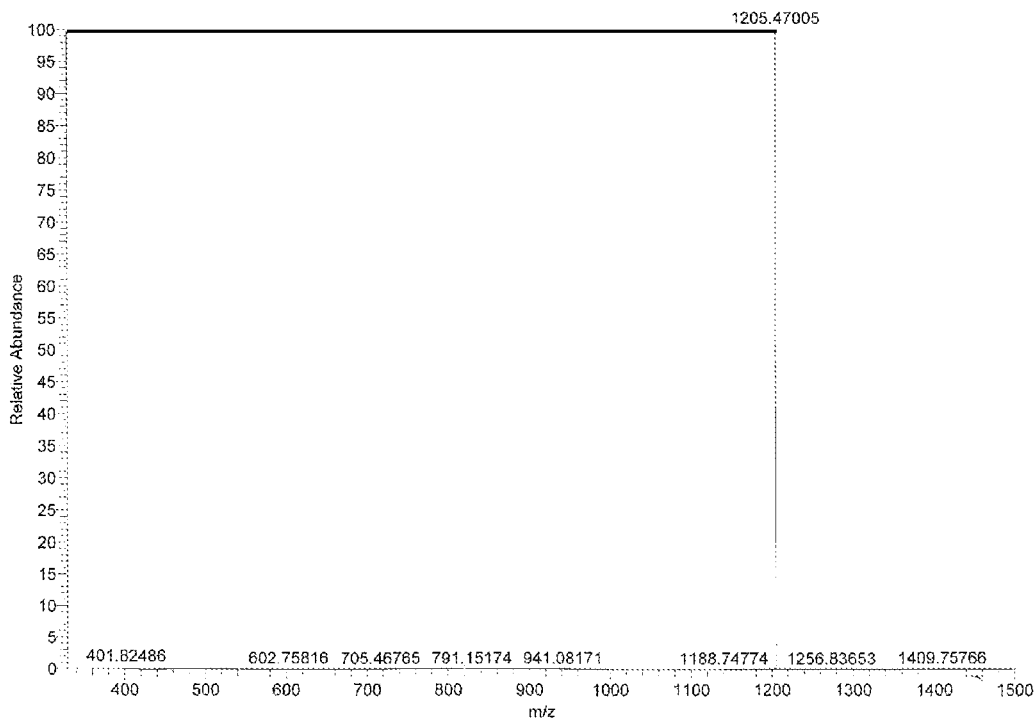
FIG. 6 depicts a high resolution Mass Spectrum of amino-β-cyclodextrin 2. Theoretical Mass: 1204.45925. Experimental Mass: 1204.47005.
Figure 7:
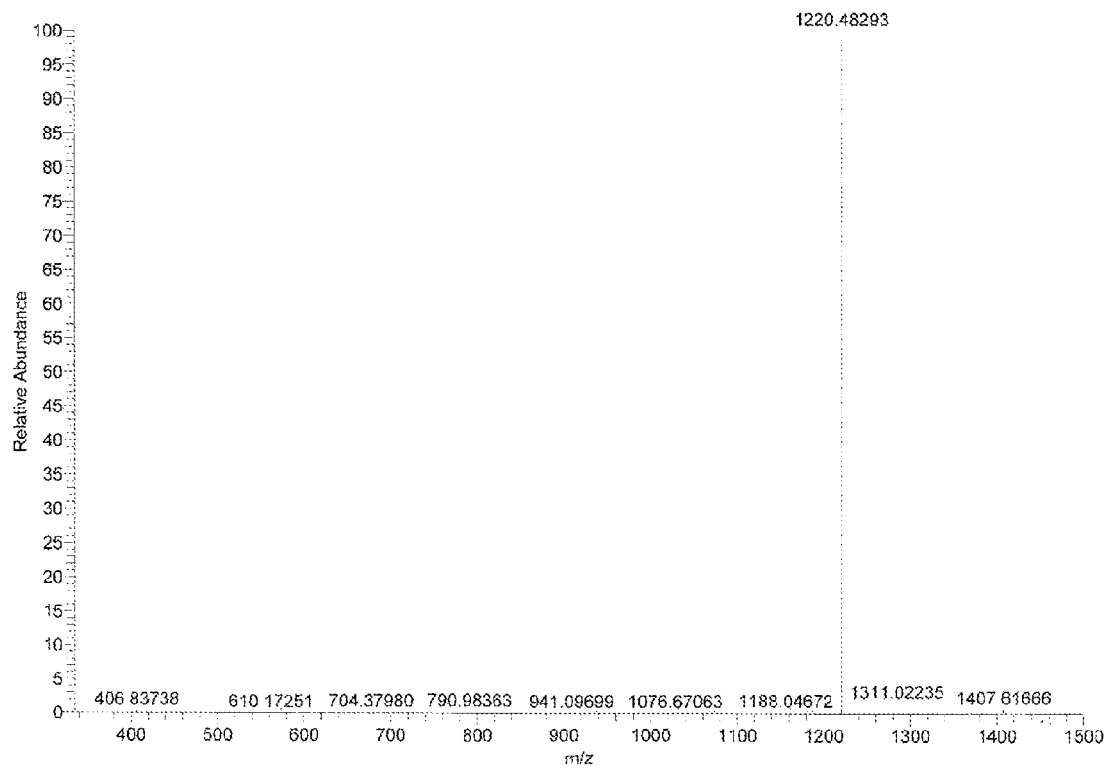
FIG. 7 depicts a high resolution Mass Spectrum of amino-β-cyclodextrin 3. Theoretical Mass: 1219.47015. Experimental Mass: 1219.48293.
Figure 8:
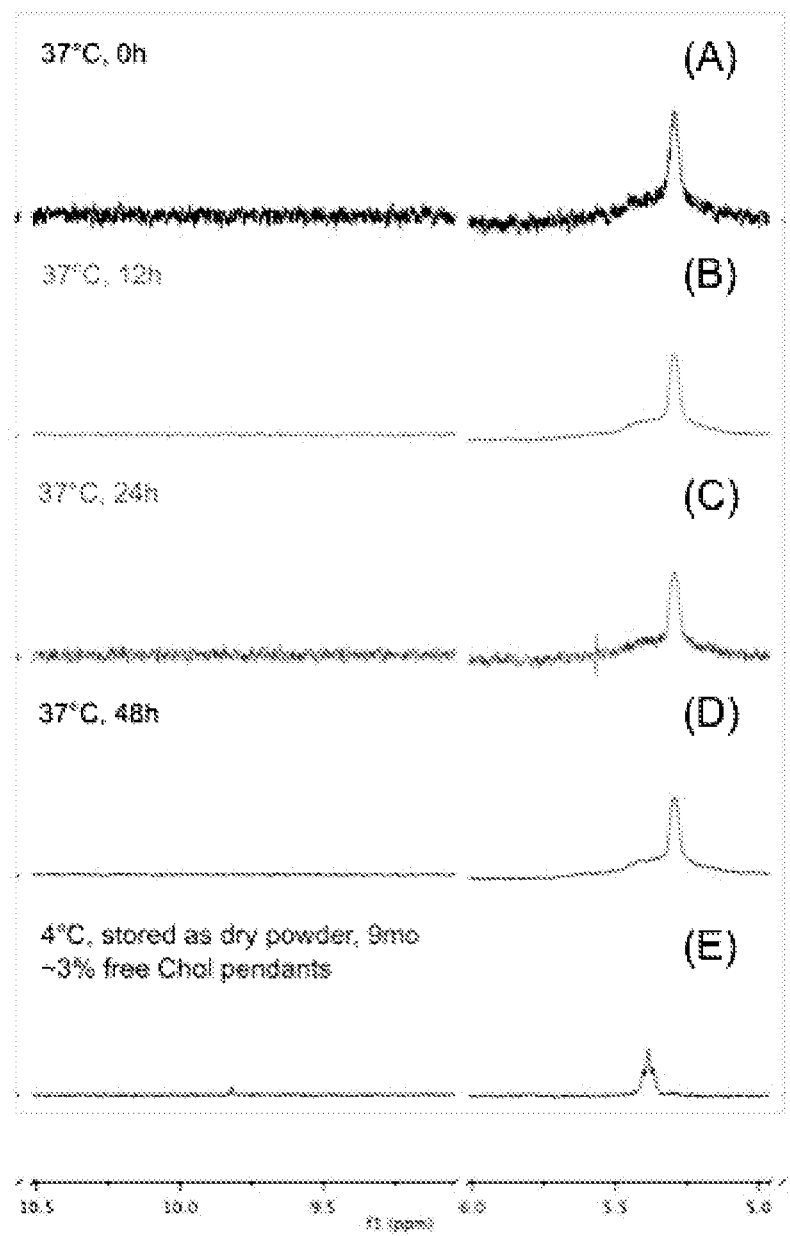
FIG. 8 depicts partial $^1$H NMR spectra (benzylidene acetal proton) of Chol-PVA-PEG at 37° C. at (A) 0 h, (B) 12 h, (C) 24 h, (D) 48 h and (E) stored as a dry powder at 4° C. for 9 months. No degradation was observed for the polymer in solution at 0° C. or 25° C. for up to 48 h.

The in vitro gene knockdown efficiency of the complexes formed between the anti-GFP siRNA and the Chol-PVA-PEG:amino-β-CD guest:host pendant polymer system was assessed in CHO-GFP cells at N/P=20 in the presence of serum (FIG. 4). The knockdown efficiencies were evaluated relative to bPEI and L2k as controls. Method A and Method B complexes both performed comparably to bPEI and L2k vectors. The lowest performing guest:host pendant polymer complexes showed gene knockdown efficiencies of ~65% and the best performing complexes showed suppression up to ~85%, depending on the amino-β-CD type. Method A and Method B complexes had similar knockdown efficiencies suggesting that the method of formulation does not appreciably affect the RNAi efficiency. Chol-PVA-PEG:1:siRNA complexes had the highest efficiency regardless of the formulation method used and performed similarly to L2k. This can be attributed to the lower charge density of 1 relative to 2 or 3, thus enabling more facile dissociation of siRNA than the other two derivatives. Studies also reveal that from the guest:host pendant polymer complex Chol is a more effective pendant group than adamantane. This enhancement is attributed to the effect that Chol has on membrane phase behavior such that endosomal escape is promoted by the pendant Chol group.

Example 14

Synthesis of hepta-6-(2'-aminoethyl)amino-β-CD (4)

Hepta-6-iodo-O-CD (1.0 g, 0.5 mmol) was dissolved in 50 mL 1,2-diaminoethane, then stirred at 60° C. under an atmosphere of $N_2$ for 24 h. The solution was then concentrated under reduced pressure to a few milliliters before pouring into acetone (300 mL). A fine white precipitate was formed and gathered by filtration. The precipitate was washed with acetone and dried under vacuum to yield a stable white powder. Yield=0.47 g (66%). $^1$H NMR (270 MHz, $D_2O$): δ=5.21-5.15 (s, 7H, C1H of CD), 4.10-3.82 (m, 21H, C3H and C5H of CD and NH) 3.77-3.54 (m, 28H, C2H, C4H and C6H of CD), 3.21-2.97 (m, 2H, N1-$CH_2$), 2.97-2.88 (t, 2H, N2-$CH_2$), 2.68-2.56 (b, 14H, $NH_2$). $^{13}$C NMR (75 MHz, $CDCl_3$): δ=102.0 (C(1) of β-CD), 82.3 (C(4) of β-CD), 73.2 (C(3) of β-CD), 72.5 (C(2) of β-CD), 72.1 (C(5) of β-CD), 55.2 (C(6) of β-CD), 53.9 (NH—$CH_2$), 45.2 ($CH_2$—$NH_2$).

Example 15

Synthesis of hepta-6-(2'-hydroxyethyl)amino-β-CD (5)

This compound was prepared as described for Compound 4, except that 2-aminoethanol was used as nucleophile instead of 1,2-diaminoethane. Yield=0.51 g (70%). $^1$H NMR (270 MHz, $D_2O$): δ=5.10-5.05 (s, 7H, C1H of CD), 4.00-3.85 (m, 14H, C3H and C5H of CD) 3.75-3.42 (m, 28H, C2H, C4H and C6H of CD), 3.01-2.82 (m, 2H, ethanolamine $CH_2O$), 2.78-2.72 (t, 2H, ethanolamine $CH_2N$). $^{13}$C NMR (75 MHz, $D_2O$): δ=104.1 (C(1) of β-CD), 84.6 (C(4) of β-CD), 74.0 (C(3) of β-CD), 73.2 (C(2) of β-CD), 72.5 (C(5) of β-CD), 67.5 ($CH_2$—OH), 58.7 (C(6) of β-CD), 57.5 ($CH_2$—N).

Example 16

Synthesis of hepta-6-hydrazyl-β-CD (6)

This compound was prepared as described for Compound 4, except that hydrazine was used as nucleophile instead of 1,2-diaminoethane. Yield=0.52 g (54%). $^1H$ NMR (270 MHz, $D_2O$): δ=5.13-5.09 (s, 7H, C1H of CD), 4.28-4.02 (b, 7H, NH), 4.02-3.22 (m, 42H, C2H, C3H, C4H, C5H and C6H of CD), 2.00-1.80 (b, 14H, $NH_2$). $^{13}C$ NMR (75 MHz, $D_2O$): δ=101.9 (C(1) of β-CD), 81.6 (C(4) of β-CD), 73.0 (C(3) of β-CD), 72.4 (C(2) of β-CD), 72.0 (C(5) of β-CD), 45.9 (C(6) of β-CD).

Example 17

Synthesis of 4-benzaldehyde adamantanecarboxyl ester (Ad-Ph-CHO)

To a solution of 4-hydroxybenzaldehyde (2.44 g, 20 mmol) in THF (10 mL) was added 3 mL $NEt_3$. The solution was cooled with ice before adding dropwise a solution of AdCOCl (5.94 g, 30 mmol) in THF (10 mL). After 6 h, the THF was removed using a rotary evaporator. The residue was dissolved in 50 mL ether and then washed three times with 1 M $Na_2CO_3$ and one time with saturated NaCl solution. The solution was dried over $Na_2SO_4$ and the solvent removed using a rotary evaporator to yield a pale yellow solid. Yield=5.11 g (90%). $^1H$ NMR (400 MHz, $CDCl_3$): δ=9.99 (s, 1H, CHO), 7.91 (d, J=8.4 Hz, 2H, ph), 7.23 (d, J=8.0 Hz, 2H, ph), 2.09-2.05 (m, 9H, Ad), 1.81-1.74 (m, 6H, Ad).

Example 18

Synthesis of Ad-PVA

PVA (MW=27 kD) (460 mg, 10 mmol) was dissolved in 10 mL dry DMSO, and then Ad-PhCHO (568 mg, 1.0 mmol) and 50 mg TSA were added. This solution was stirred for 2 d at 50° C. The solution was then poured into acetone (300 mL). A fine white precipitate was formed and gathered by filtration. The precipitate was washed with acetone and dried under vacuum to yield a stable white solid. Yield=850 mg (85.2%). $^1H$ NMR (400 MHz, $d_6$-DMSO): δ=7.42 (w, 2H, Ph), 7.03 (w, 2H, Ph), 5.51 (s, 1H, PhCH), 4.66-4.02 (m, 3H, PVA-OH), 3.96-3.74 (m, 5H, PVA-CH), 2.02-1.95 (m, 9H, Ad), 1.70 (m, 6H, Ad), 1.59-1.21 (m, 10H, PVA-$CH_2$).

Example 19

Synthesis of Ad-PVA-PEG

A solution of CDI (162 mg, 1 mmol in 10 mL DMSO) was added dropwise to a solution of Ad-PVA (720 mg in 20 mL DMSO). The solution was stirred for 1 d at 50° C., then processed by addition of 300 mL dry THF three times to precipitate the CDI-activated polymer, which was used directly in the next step after re-dissolving in 10 mL DMSO. After the addition of methoxypolyethylene glycol amine (MW=750 or 2000) $NH_2$—PEG-OMe (750 mg, 100 eq, 1 mmol of PEG750; or 6.4 g, 320 eq, 3.2 mmol of PEG2000) to the solution, the reaction was stirred overnight. The product was dialyzed against DMSO and deionized water three times (Spectra/Por Membrane, MWCO 6000-8000) to remove low MW impurities. After removal of the solvent, the polymer was redissolved in DMSO and precipitated into acetone. The Ad-PVA-PEG was isolated as a pale yellow solid. Yield=1.1 g. $^1H$ NMR (400 MHz, $H_2O$): δ=7.61-7.45 (br, Ph), 7.12-7.01 (br, Ph), 5.2-4.6 (br m, PVA-OH, overlapped with HDO), 4.01-3.05 (br m, PVA-CH and PEG-$CH_2$), 2.2-1.5 (br, Ad). MW Ad-PVA-$PEG_{750}$=112 kDa; MW Ad-PVA-$PEG_{2000}$=645 kDa.

Example 20

$^1H$ NMR Evidence for Acid Catalyzed Cleavage of Acetal Linker

Ad-PVA (50 mg) was dissolved by sonication in 2 mL of 10 mM β-CD $D_2O$ solution for 10 min, followed by removal of undissolved material via centrifugation at 5400 rpm for 1 h. The sample was the transferred to an NMR tube for analysis. Trifluoroacetic acid (TFA) was added to get the desired pH (pH=4 and pH=7), and the $^1H$NMR spectra recorded at 4 h and 48 h.

Example 21

Synthesis of Amino-β-$CD^+$ and Ad-PVA-PEG Host:Guest Polymer Components

Figure 14:
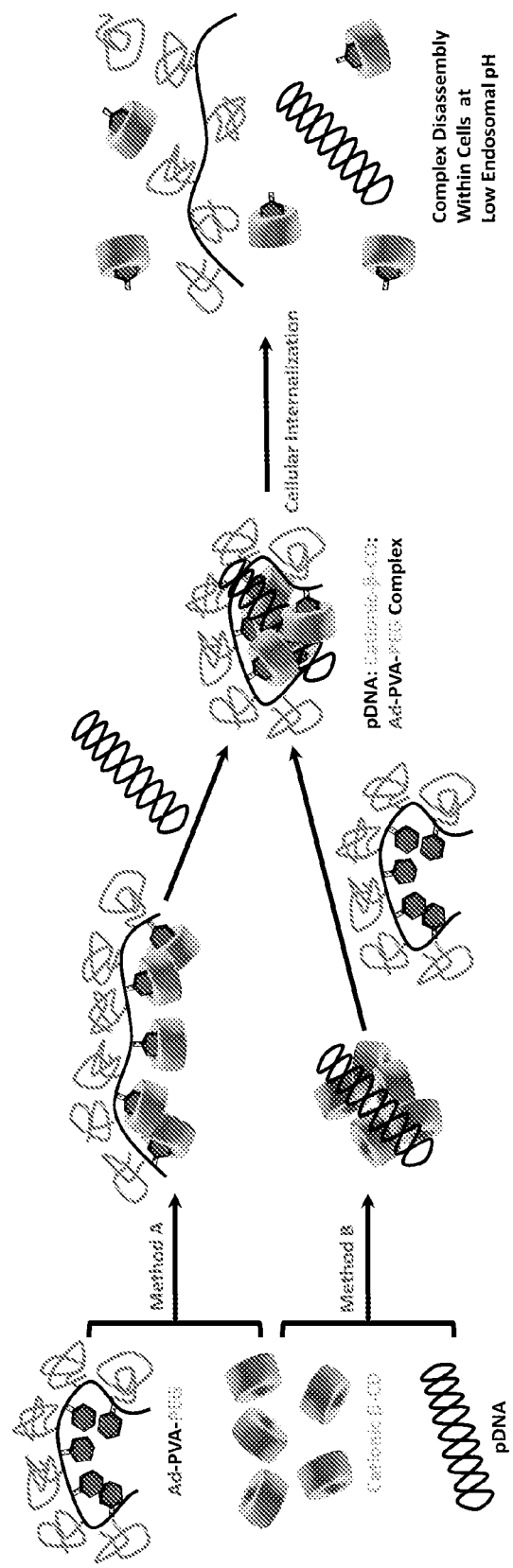
FIG. 14 depicts a conceptual diagram of pDNA:amino-β-CD:Ad-PVA-PEG complexation.
Figure 15:
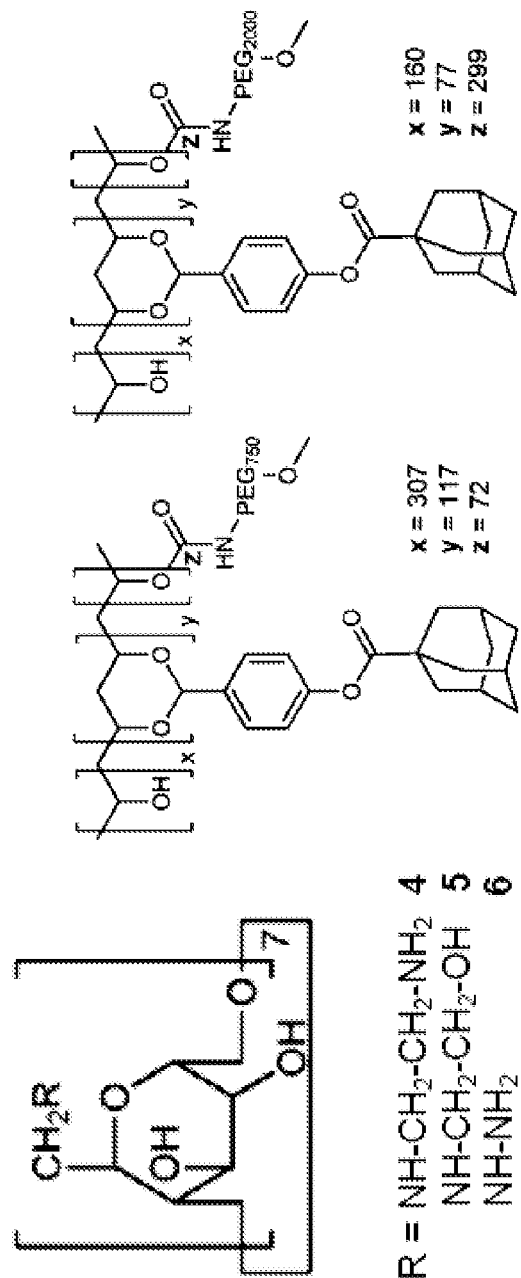
FIG. 15 depicts structures of amino-β-CDs, Ad-PVA-PEG750 and Ad-PVA-PEG2000.
Figure 16:
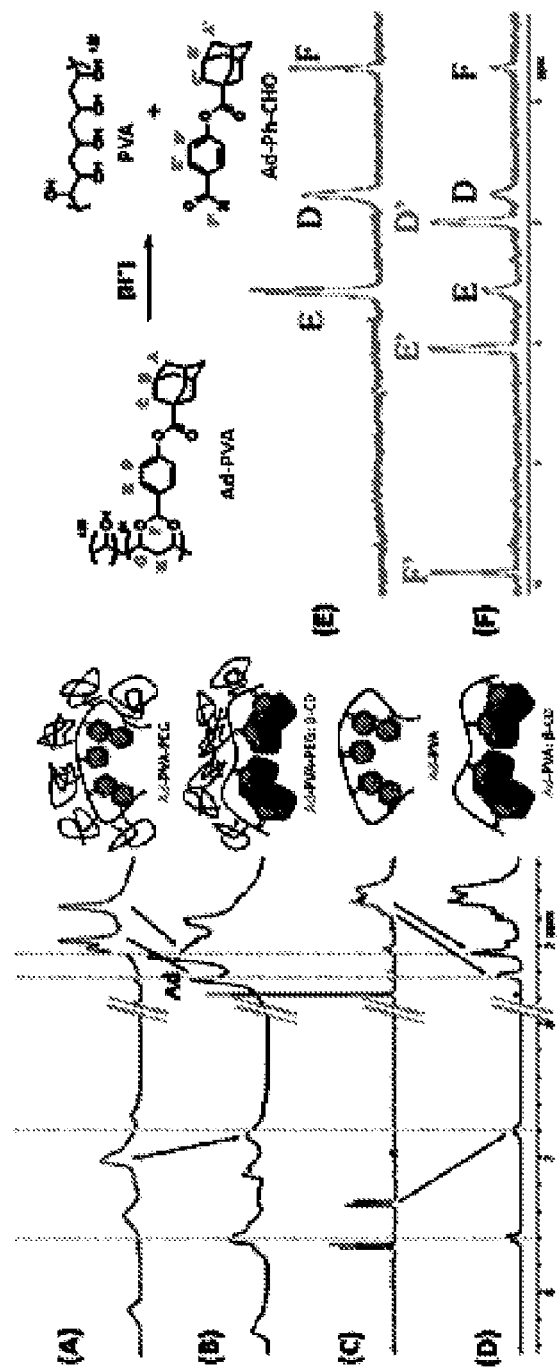
FIG. 16 depicts 400 MHz $^1$H NMR spectra of Ad-PVA-PEG in the absence (A), in the presence (B) of β-CD; Ad-PVA in the absence (C), and presence (D) of β-CD in $D_2O$ at 20° C., and Ad-PVA with β-CD at pH=7 (E) and pH=4 (F) in $D_2O$ at 20° C.

Based on the design shown in FIG. 14, three cationic β-CD derivatives (FIG. 15) were synthesized to test the amino-β-$CD^+$:pendant polymer concept, i.e., hepta-6-(1',2'-diaminoethyl)-β-CD (4), hepta-6-(2'-hydroxyethylamino)-β-CD (5), and hepta-6-(hydrazino)-β-CD (6). The amino-β-$CD^+$ components were synthesized from hepta-6-iodo-β-CD by a simple one step procedure. Ad-PhCHO was prepared from 4-hydroxybenzaldehyde and 1-adamantane carbonyl chloride. Ad-PhCHO was further used to synthesize Ad-PVA and Ad-PVA-PEG from PVA (27 kD). The Ad-PVA was prepared from Ad-PhCHO and PVA in the presence of a catalytic amount of TSA to give the acetal-based pendant polymer. Ad-PVA was isolated by precipitation in acetone. This was further activated by 1,1'-carbonyldiimidazole to give the PEGylated pendant polymer, Ad-PVA-PEG. The Ad-PVA and Ad-PVA-$PEG_{750}$ were prepared with 19 mol % Ad acetal modifications and 12 mol % PEG750 carbamate modifications (MW=112 kDa), while Ad-PVA-$PEG_{2000}$ was prepared with 13 mol % Ad acetal modifications and 48 mol % PEG2000 carbamate modifications (MW=645 kDa) as determined by $^1H$ NMR. These pendant polymer constructs then were investigated for their ability to promote pDNA:host:guest complex formation and acid-responsive disassembly.

Example 22

Characterization of Amino-β-$CD^+$:Ad-PVA-PEG Interaction

Figure 21:
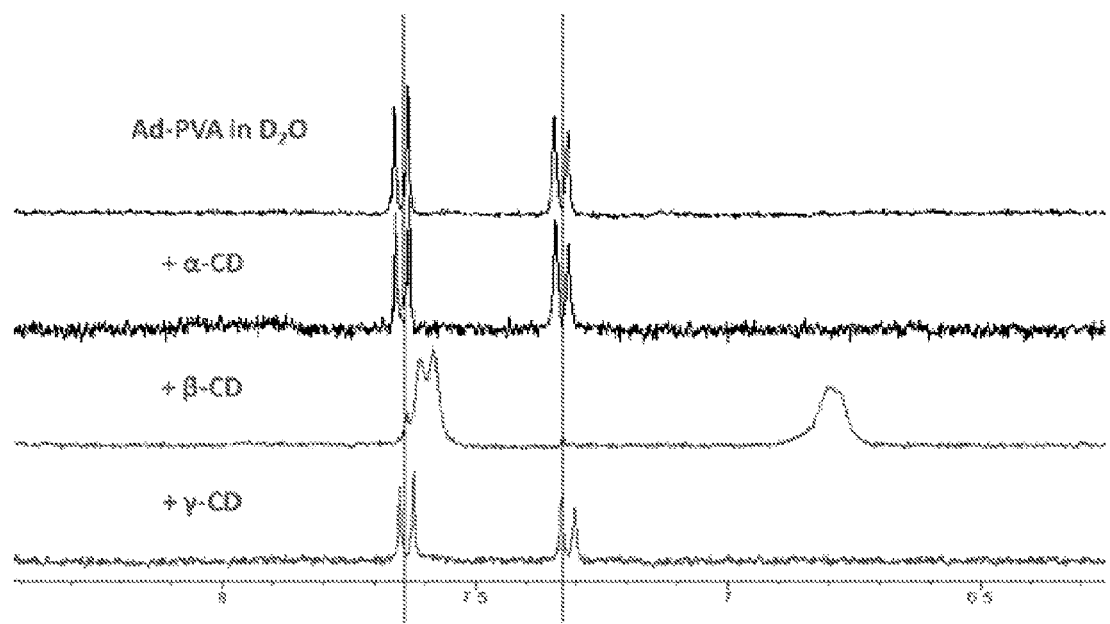
FIG. 21 depicts 300 MHz $^1$H NMR spectra of Ad-PVA with α-CD, β-CD and γ-CD in $D_2O$ at 20° C.
Figure 22:
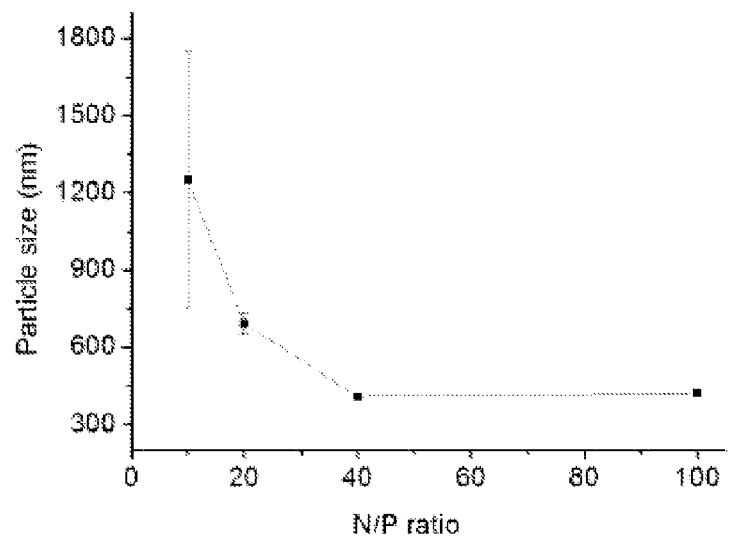
FIG. 22 depicts particle sizes of pDNA:5:Ad-PVA-PEG$_{750}$ complexes formulated by Method A.

Complexation of Ad-PVA and Ad-PVA-$PEG_{750}$ with the amino-β-$CD^+$ derivatives was confirmed by $^1H$ NMR (FIGS. 16A-16D). In one aspect, the phenyl and Ad resonances of the PVA derivatives showed upfield shifts upon the addition of amino-β-CD host ligands in aqueous media, indicating the formation of host:guest polymer complexes via Ad:CD inclusion. The complexation of the pendant polymer with α-CD and γ-CD as studied by $^1H$ NMR revealed that there was no detectable binding of the α-CD or γ-CD to the polymer (i.e., no upfield shift was observed for the phenyl or Ad resonances upon their addition to the aqueous solution of the pendant polymer (FIG. 21). Next, the acid-catalyzed cleavage of the acetal bond used to connect the Ad guest ligand to the polymer backbone was tested. $^1$H NMR spectra of Ad-PVA in D$_2$O in the presence of equimolar unmodified β-CD was measured as a function of pH. At pH=7, the resonances of the benzylidene acetal pendant group protons were observed at 7.6, 6.8 and 5.6 ppm. After treating this solution at pH=4 for 48 h, the $^1$H NMR spectra exhibited three new peaks at 7.0, 8.1, and 9.8 ppm that were attributed to the cleaved benzaldehyde-4-adamantane carboxyl ester unit (FIGS. 16E and 16F). Detailed hydrolysis kinetics was studied by a pyrene fluorescence assay to study the time-dependent degradation of the polymer. Evidence from NMR and the pyrene fluorescence assay of the pendant group cleavage from the polymer main chain at low pH suggests that a similar process may occur upon cellular internalization. Hydrolysis of the pendant groups from the PVA backbone within the acidic endosomal environment would be expected to promote complex disassembly, pDNA un-packaging and escape.

Zeta Potentials

Figure 17:
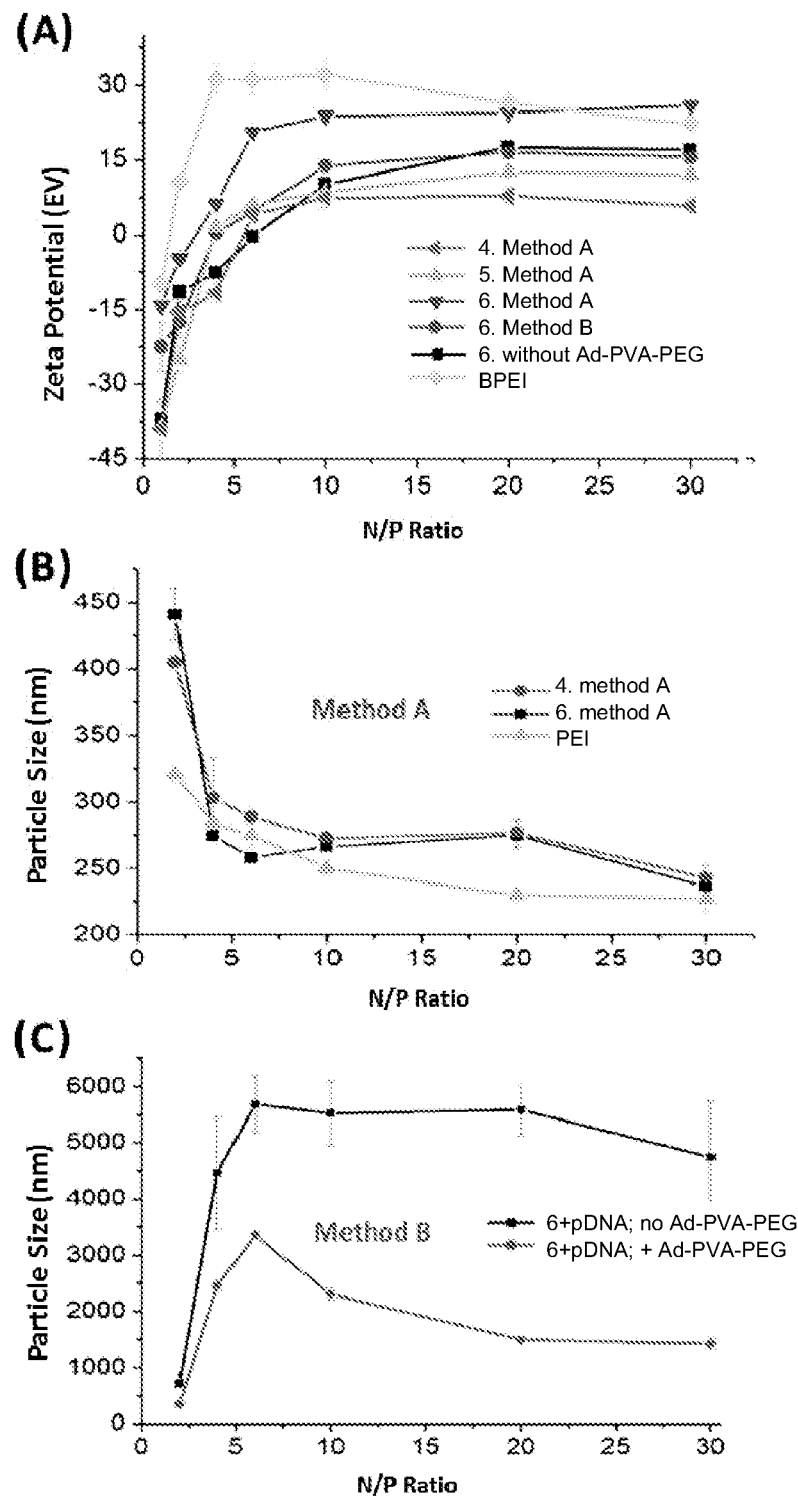
FIG. 17 depicts (A) Zeta potential measurements of pDNA:amino-β-CD complexes and pDNA:bPEI complexes, DLS Measurements of (B) pDNA:4:Ad-PVA-PEG$_{750}$ and pDNA:6:Ad-PVA-PEG$_{750}$ complexes formulated by Method A and (C) pDNA:6 and pDNA:6:Ad-PVA-PEG$_{750}$ complexes formulated by Method B.

Zeta potentials were measured for both types of complexes with Ad-PVA-PEG$_{750}$ to determine the surface charge of the resulting transfection particles (FIG. 17). It is observed that complexes formed by both methods, as well as polymer-free amino-β-CD$^+$:pDNA complexes, had positive ζ, when N:P>5. Hydrazine derivative 6 was an unusual case in that complexes of this species prepared either via Method B or in the absence of Ad-PVA-PEG$_{750}$ gave similar results, whereas complexes of 6 produced using Method A had a positive charge that was significantly higher and comparable to bPEI:pDNA complexes. In one aspect, observe that complexes formulated from Ad-PVA-PEG$_{2000}$ have a surface charge that is slightly negative. Similar trends were observed with Ad-PVA-PEG such complexes formulated with 6 produced nearly neutral surface charges at N:P=20.

TABLE 3

Zeta Potentials of Formulations with Ad-PVA-PEG

| Formulation with Ad-PVA-PEG$_{750}$ | Zeta Potentials (mV) | | | | |
|---|---|---|---|---|---|
| | N:P = 5 | N:P = 10 | N:P = 15 | N:P = 20 | N:P = 30 |
| 1, Method B | −17 ± 1.3 | −2.2 ± 0.1 | 1.3 ± 0.5 | 3.0 ± 0.8 | 3.1 ± 0.5 |
| 1 without Ad-PVA-PEG | −14.5 ± 0.5 | −0.3 ± 0.2 | 2.6 ± 0.1 | 3.2 ± 0.6 | 2.8 ± 0.7 |
| 2, Method B | −2.3 ± 0.9 | 3.8 ± 1.1 | 4.1 ± 0.3 | 6.1 ± 0.2 | 6.3 ± 0.1 |
| 2 without Ad-PVA-PEG | −1.1 ± 0.1 | 4.1 ± 0.8 | 3.6 ± 0.3 | 7.2 ± 0.4 | 7.1 ± 0.2 |

Example 23

Characterization of the Particles Formed by pDNA:Amino-β-CD$^+$:Ad-PVA-PEG Complexation The ability of these non-covalent pendant polymer assemblies to condense pDNA was then evaluated with respect to particle size and net charge. Two different complexation methods (FIG. 14) were used to evaluate the relative capacity of amino-β-CD$^+$:Ad-PVA-PEG$_{750}$ host:guest polymer assemblies toward pDNA condensation. In Method A, Ad-PVA-PEG$_{750}$ was pre-associated with amino-β-CM before addition to the pDNA solution. In Method B, the pDNA was first complexed with the respective amino-β-CD$^+$, followed by addition of Ad-PVA-PEG$_{750}$.

Gel Shift Assays

Gel shift assays of pDNA complexes with the amino-β-CD$^+$ and the amino-β-CD$^+$:Ad-PVA-PEG$_{750}$ pendant polymer assemblies indicate that both methods of formulation had comparable pDNA complexation abilities. Also, in the absence of polymer, higher N:P ratios were used to condense pDNA effectively. Comparison of the three amino-β-CD$^+$ compounds indicated that 6 has the greatest capacity for condensing pDNA compared to 4 and 5. This improved condensation capability of 6 relative to 4 and 5 can be attributed to the availability of both the nitrogens on the hydrazine moiety for interaction with pDNA. In case of 4 and 5, the more basic 2° amines are not as easily accessible to the pDNA, resulting in less effective condensation.

Dynamic Light Scattering

Dynamic light scattering (DLS) was used to determine the transfection complex sizes produced using these different materials and methods. The data show that both 4 and 6 had plasmid condensation abilities that were similar to bPEI when Method A was used (i.e., the particle diameters were below 300 nm when N:P>5) (FIG. 17B). Compound 5 also condensed pDNA to form particles of ~400 nm at high N:P ratios (>40) using Method A (Table 4). In stark contrast, Method B complexes of 6:pDNA showed a sharp increase in particle size across a narrow N:P ratio range of 2:1→5:1 (500-5500 nm), indicating that extensive aggregation occurs with these complexes in the absence of polymer. Interestingly, the particle sizes of pDNA:6:Ad-PVA-PEG$_{750}$ complexes initially increased over this same range of N:P ratios, followed by a decrease to below 2000 nm at N:P>10. The PEG-grafted polymer helps to sterically stabilize the 6:pDNA particles (FIG. 17C). Findings indicate that Method A is preferential to Method B for producing small transfection complexes, presumably due to improved steric stabilization and a reduced propensity for Ad-PVA-PEG$_{750}$ to promote particle aggregation via host:guest interactions of a single polymer chain between two or more pre-formed amino-β-CD$^+$:pDNA particles. DLS measurements of complexes made with Ad-PVA-PEG$_{2000}$ showed that the particles were less than 300 nm for the CD variants. Ad-PVA-PEG complexes prepared by Method B were larger than those prepared by Method A. Notice that at similar N:P ratios (e.g., 20), complexes formulated from Ad-PV A-PEG$_{2000}$ are significantly smaller than those prepared from Ad-PVA-PEG$_{750}$ (225 vs. 295 nm, respectively, for 4). This indicates that the increased PEG MW and grafting density on the polymer backbone sterically stabilizes the complexes and helps condense them into smaller particles (Table 4).

TABLE 4

Particle Sizes and Zeta Potential Measurements of pDNA:Amino-
β-CD$^+$:Ad-PVA-PEG$_{2000}$ Complexes at N:P = 20

| Amino-β-CD | Method of Formulation | Size (nm) | PDI | Zeta Potential ζ (mV) |
|---|---|---|---|---|
| 1 | A | 224.5 | .39 | −8.1 ± 0.1 |
|   | B | 325.0 | .40 | −10.7 ± 0.7 |
| 2 | A | 192.6 | .33 | −6 ± 0.4 |
|   | B | 280.8 | .32 | −6 ± 0.4 |
| 3 | A | 343.1 | .36 | −9.2 ± 0.5 |
|   | B | 293.1 | .30 | −5.9 ± 0.6 |

AFM Images

Figure 18:
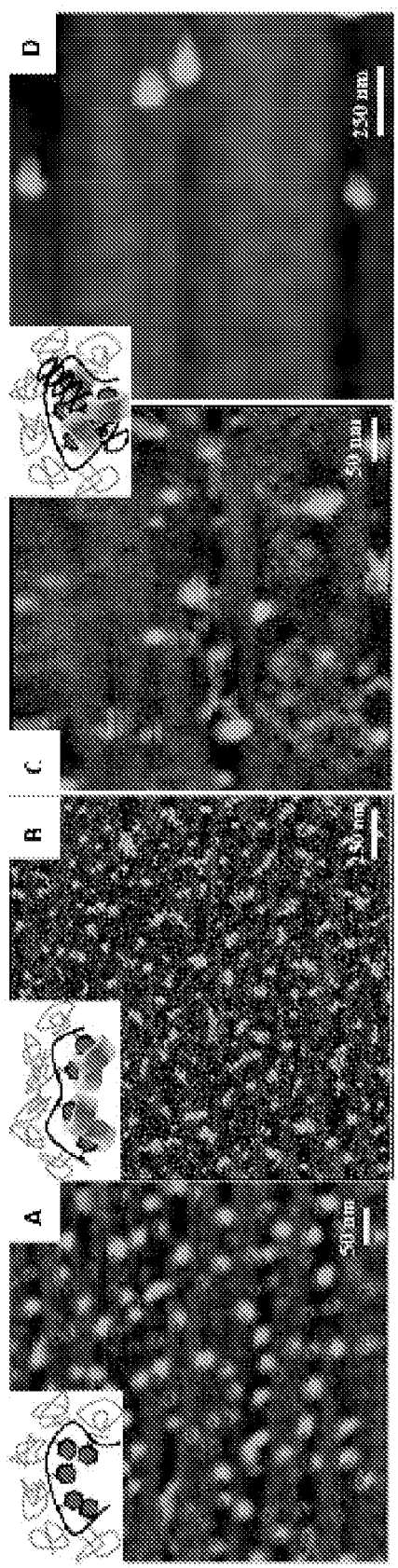
FIG. 18 depicts AFM images of (A) Ad-PVA-PEG$_{750}$ and (B) 1:1 β-CD:Ad-PVA-PEG$_{750}$. Images of pDNA:6:Ad-PVA-PEG$_{750}$ prepared by Method B at (C) N:P=2 and (D) N:P=6. The insets illustrate the possible structures in these images. The samples were prepared by adding a drop of solution to the mica surface and then slowly evaporating the sample at 25° C. overnight.
Figure 23:
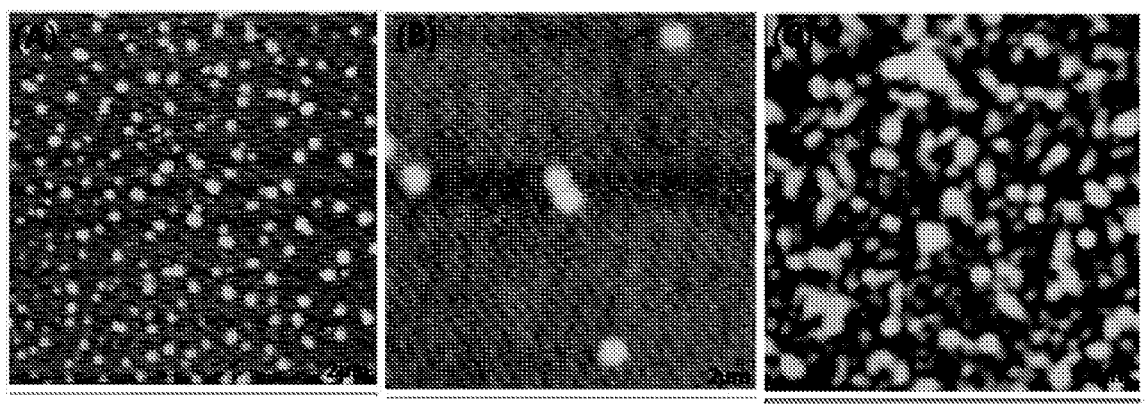
FIG. 23 depicts AFM images of (A) Ad-PVA-PEG$_{2000}$; (B) 1:1 β-CD:Ad-PVA-PEG$_{2000}$; and pDNA:6:Ad-PVA-PEG$_{2000}$, prepared by Method B at (C) N:P=2. The samples were prepared by adding a drop of solution to the mica surface and then slowly evaporating the sample at 25° C. overnight.
Figure 24:
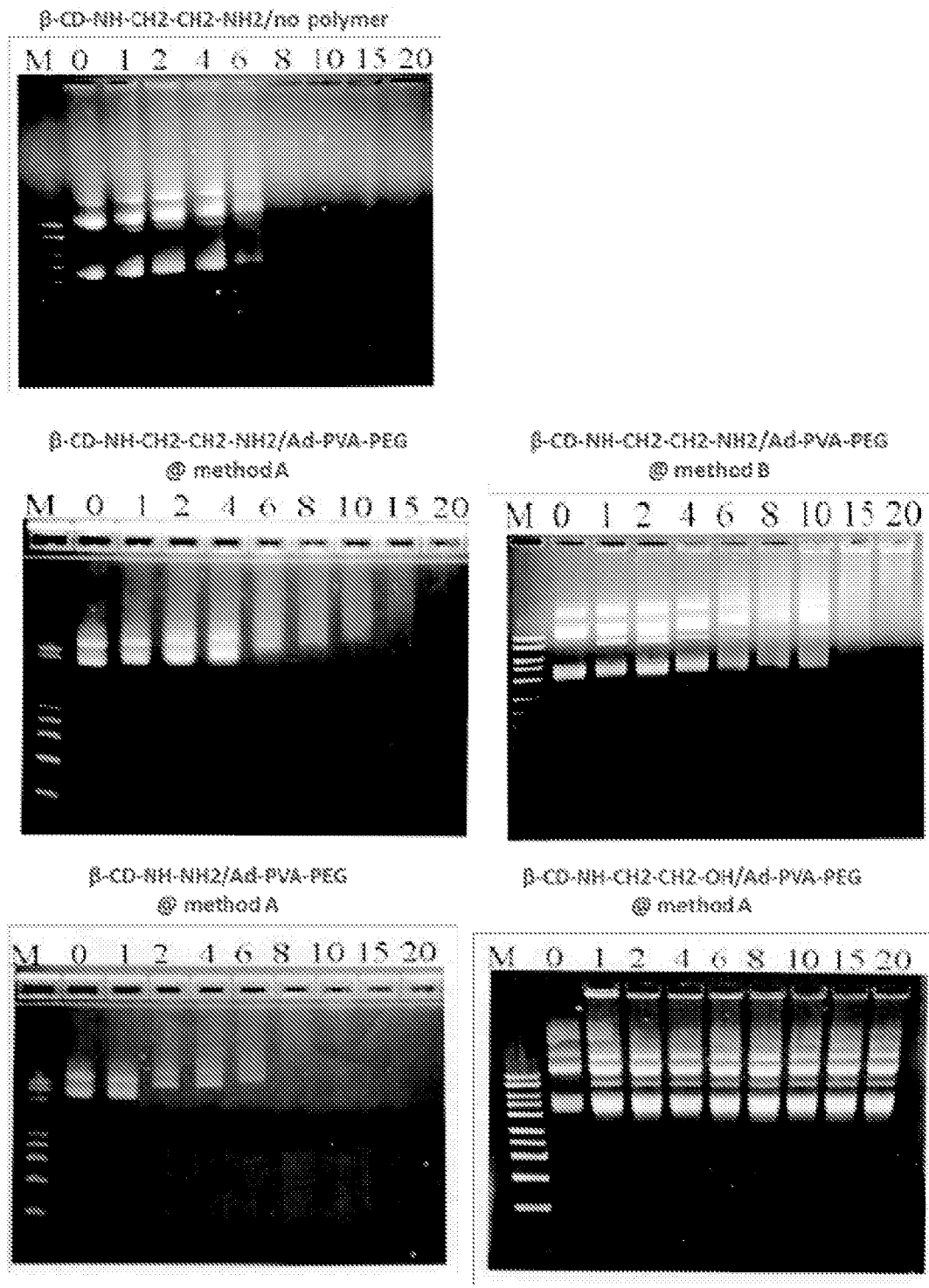
FIG. 24 depicts a gel shift assay of amino-β-CD:Ad-PVA-PEG transfection complexes at various N:P ratios. Images showed pDNA condensation capabilities of 4:no polymer, 4:Ad-PVA-PEG @ Method A, 4:Ad-PVA-PEG @ Method B, 6:Ad-PVA-PEG @ Method A, and 5:Ad-PVA-PEG @ Method A.
Figure 25:
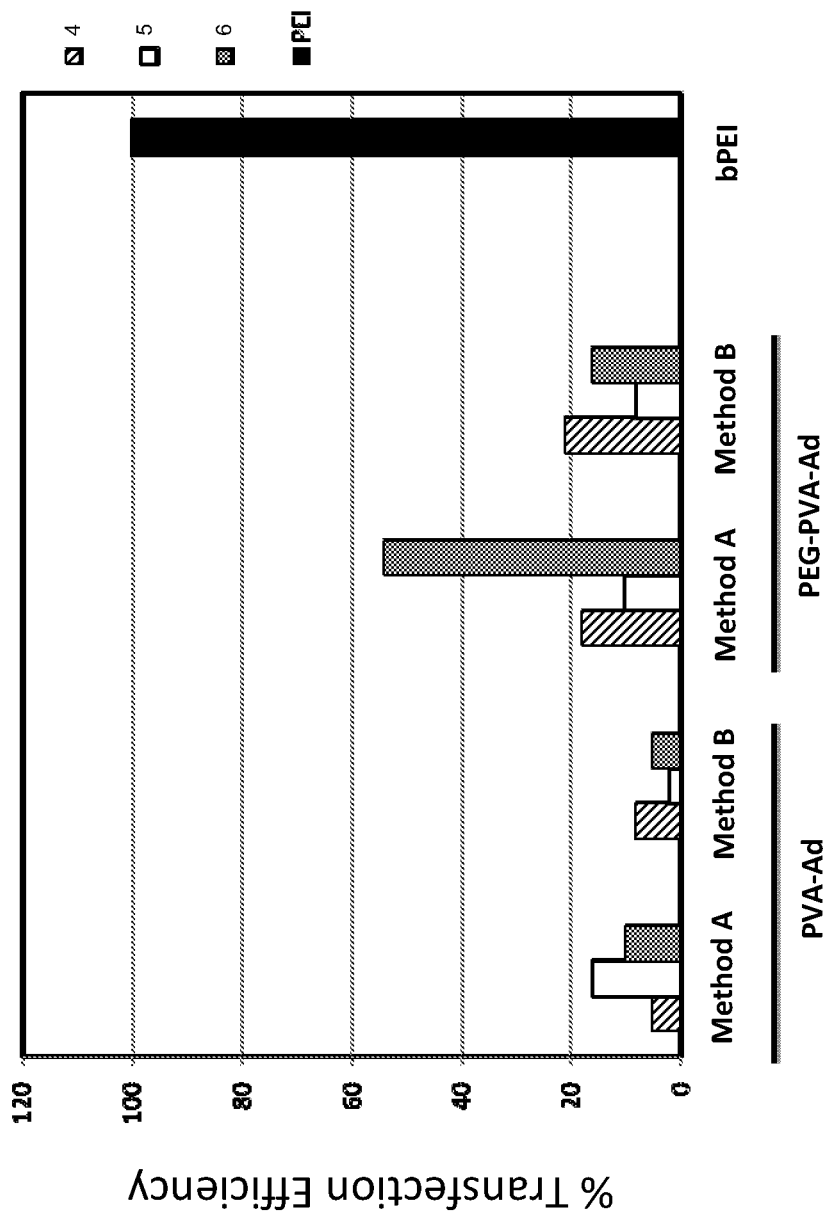
FIG. 25 depicts in vitro gene transfection efficiencies of the complexes of pDNA:amino-CD$^+$:Ad-PVA and Ad-PVA-PEG$_{750}$ relative to PEI (25K) at N:P=20 in serum free media in HeLa cells.
Figure 26:
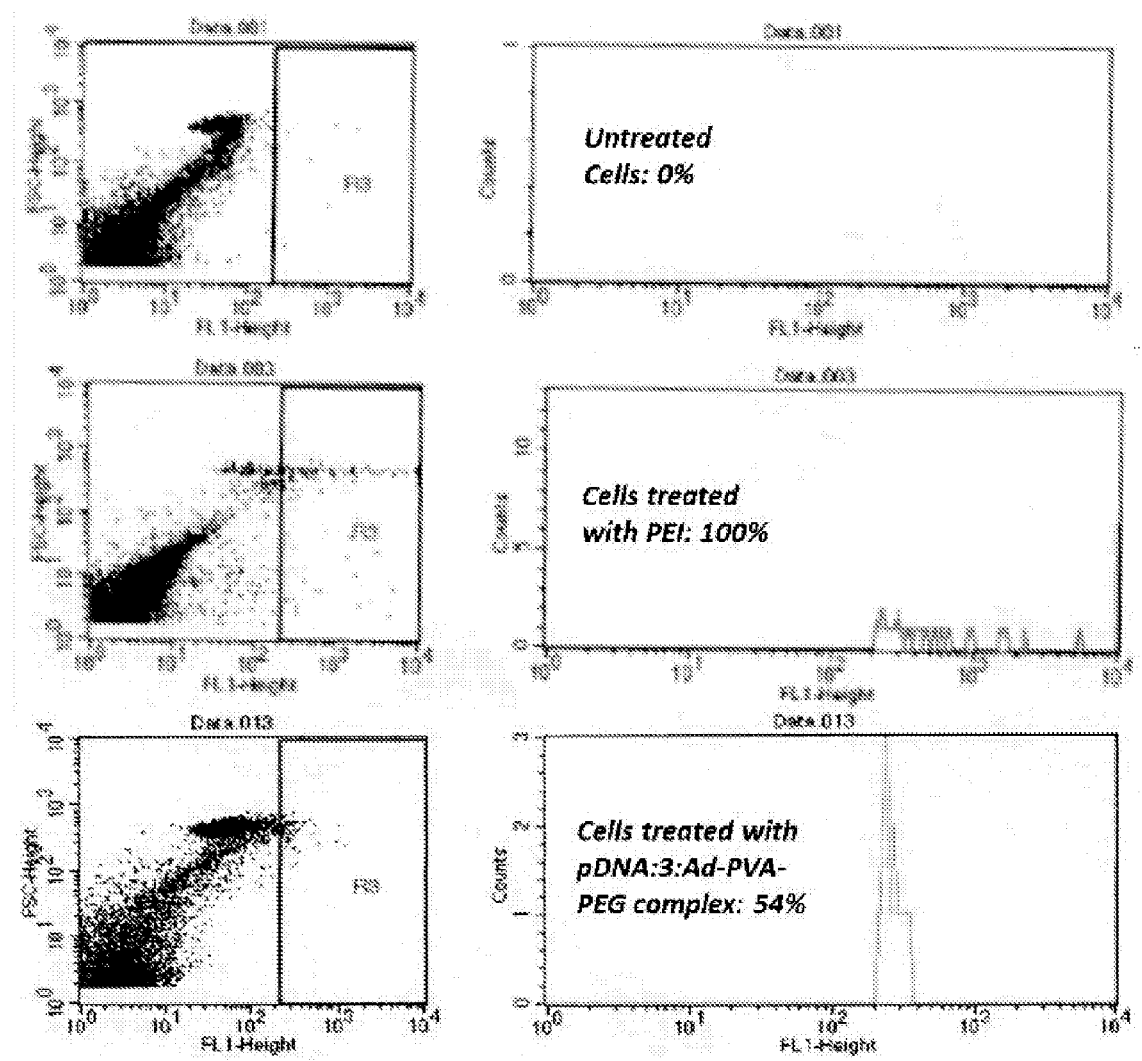
FIG. 26 depicts a flow cytometric analysis of plasmid DNA encoding mhGFP plasmid in HeLa cells. Comparison of complex of pDNA:6:Ad-PVA-PEG$_{750}$ relative to pDNA:PEI (25 kD) at N:P=20 in serum free media using HeLa cells (2 μg/well pDNA).
Figure 27:
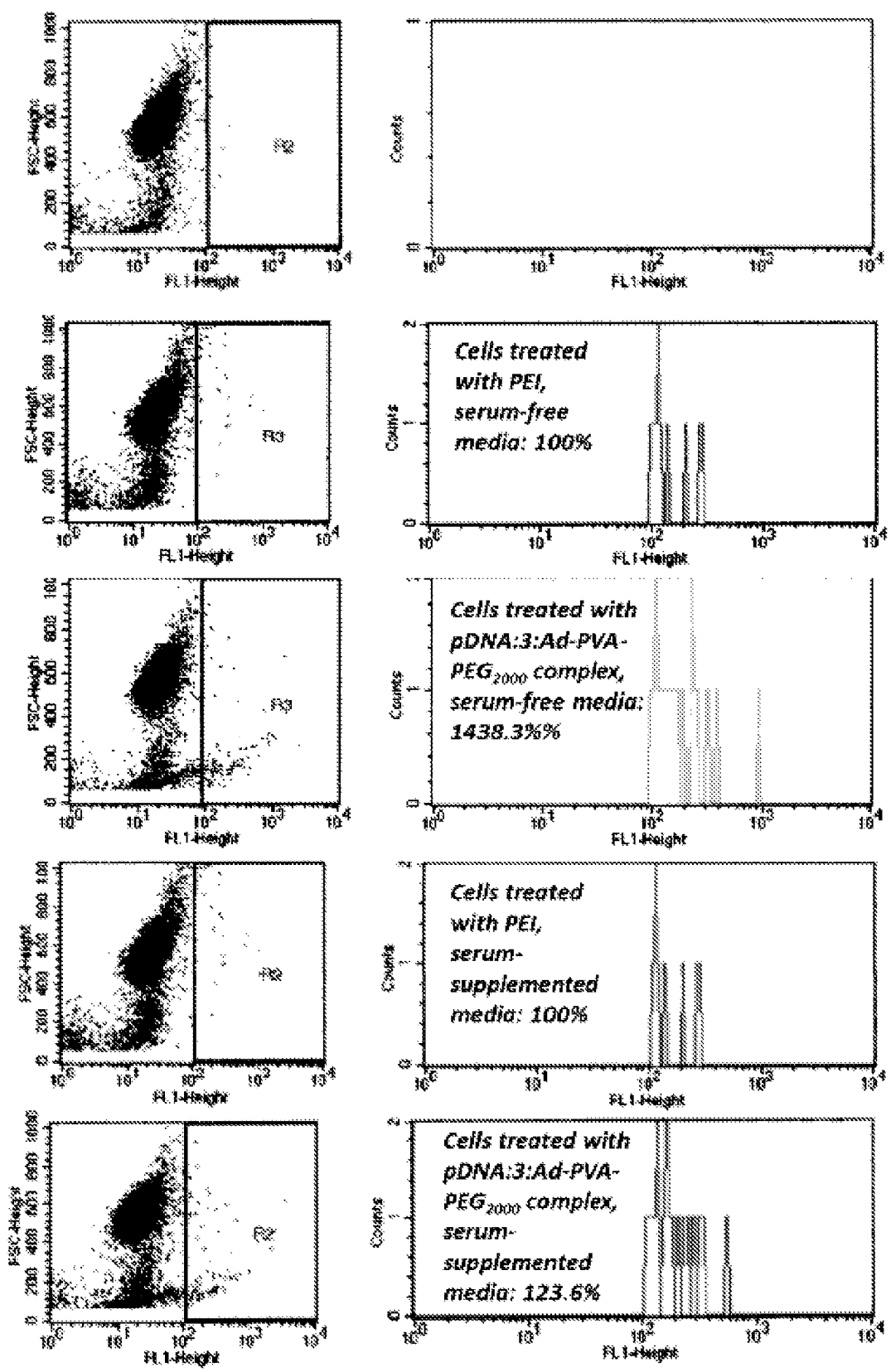
FIG. 27 depicts a flow cytometric analysis of plasmid DNA encoding mhGFP plasmid in HeLa cells. Comparison of complex of pDNA:6:Ad-PVA-PEG$_{2000}$ relative to pDNA:PEI (25 kD) at N:P=20 in serum-free and serum-supplemented media using HeLa cells (2 μg/well pDNA).

AFM images of Ad-PVA-PEG$_{750}$ samples revealed the presence of spherical to particles (FIG. 18A) that were formed by aggregation of the pendant Ad units in aqueous media. Upon addition of amino-β-CD$^+$ derivatives, the spherical particles were transformed into granular fibrillar shaped objects (FIG. 18B). From these observations it can be inferred that β-CD complexation with the polymer Ad groups via host:guest interaction causes a transformation of the spherical micelle geometry to an elongated, flexible rod structure due to the combined effects of electrostatic repulsion between the neighboring cationic amino-β-CD$^+$s that are appended to the polymer backbone via host:guest inclusion and the excluded volume occupied by the pendant PEG750 segments. When pDNA was added to this system at low N:P ratios, the samples were observed to be a mixture of fibers and particles, presumably due to the presence of both partially-complexed flexible rod structures and more partially compacted pDNA complexes (FIG. 18C). When N:P=6, particles with diameters of about 100 nm were observed (FIG. 18D). Ad-PVA-PEG$_{2000}$ formed complexes that were smaller than the complexes formed by Ad-PVA-PEG$_{750}$, but showed similar trends with respect to shape and morphology (FIG. 23). The sizes determined by AFM are smaller than those measured by DLS due to the absence of solvent-swollen polymer in the AFM samples. These results support the conclusion that host:guest complexation of Ad-PVA-PEG with amino-β-CD$^+$ produces a non-covalent assembly that is capable of condensing pDNA into compact, relatively uniform particles that are sufficiently small to be internalized by cells via endocytosis.

Example 24

Figure 19:
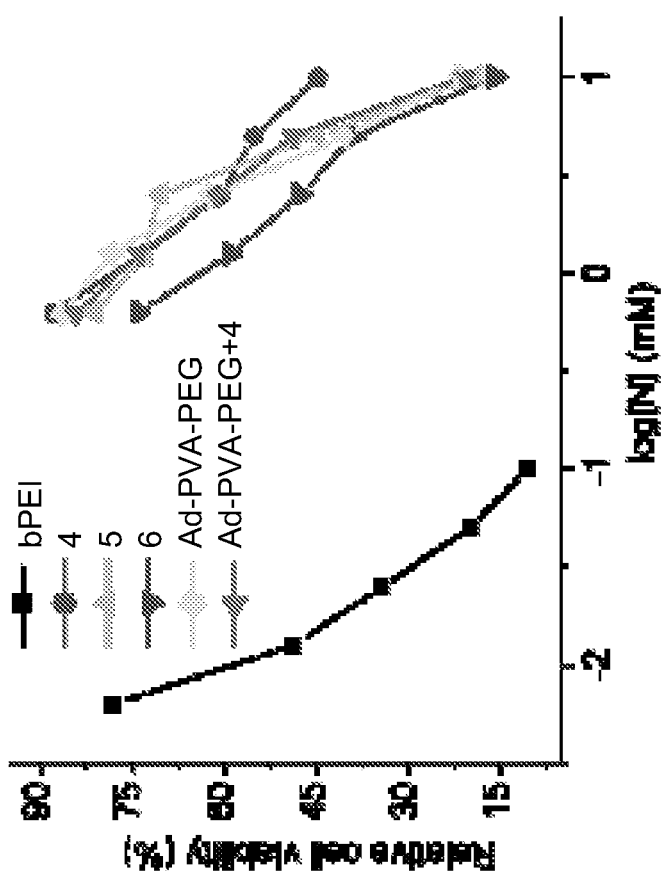
FIG. 19 depicts cytotoxicities of 4, 5, 6, Ad-PVA-PEG$_{750}$ and 4:Ad-PVA-PEG$_{750}$ host:guest complexes in HeLa cells using 25 kD bPEI as a control. The cells were treated with increasing concentrations of amino-β-CDs, 4:Ad-PVA-PEG$_{750}$ complexes, and bPEI for 24 h in serum-free media before analysis by MTT assay.

Acute Cytotoxicity and Transfection Properties of Amino-β-CD$^+$:Ad-PVA-PEG Complexes The in vitro cytotoxicity of amino-β-CD$^+$s, Ad-PVA-PEG$_{750}$, and their host:guest complexes are a highly relevant factor for their long term consideration as a safe non-viral nucleic acid vector. FIG. 19 shows that Ad-PVA-PEG$_{750}$, the amino-β-CD$^+$s, and the 4:Ad-PVA-PEG$_{750}$ host:guest complex were nearly three orders of magnitude less cytotoxic than bPEI, a benchmark reagent for in vitro and in vivo transfections. The LD50's of bPEI, 4, 5, 6, Ad-PVA-PEG and 1:1 4:Ad-PVA-PEG$_{750}$ were 0.01 mM, 4.5 mM, 8.9 mM, 1.6 mM, 1.77 mM and 2 mM, respectively.

Figure 20:
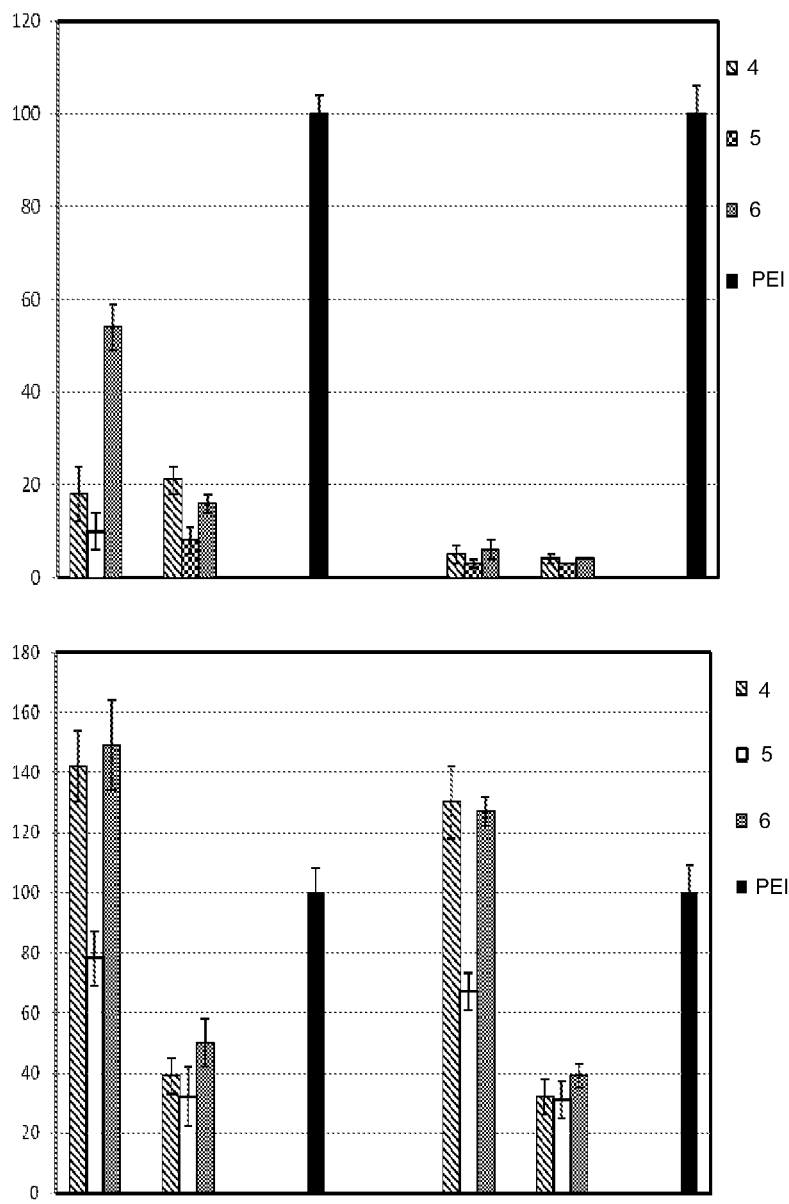
FIG. 20 depicts in vitro transfection efficiencies of amino-β-CD host:guest complexes with (A) Ad-PVA-PEG$_{750}$ and mhGFP pDNA (B) Ad-PVA-PEG$_{2000}$ and mhGFP pDNA in HeLa cells; with 25 kD bPEI (control) considered as 100% transfection efficiency. Fluorescence microscope images of transfected HeLa cells (C) bPEI 25k, (D) 6:Ad-PVA-PEG$_{750}$ using Method A at N:P=20 in serum-free media using GFP gene as a reporter gene; scale bar: 100 μm.
Figure 20:
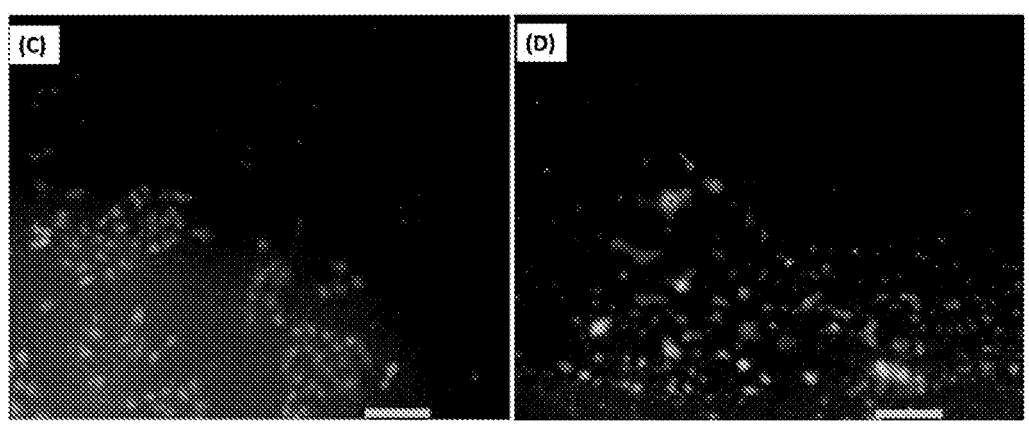

The in vitro performance of the transfection complexes generated by complexation of pDNA (mhGFP) and the amino-β-CD$^+$:Ad-PVA, amino-β-CD$^+$:Ad-PVA-PEG$_{750}$ or amino-β-CD$^+$:Ad-PVA-PEG$_{2000}$ host:guest pendant polymer systems were assessed in HeLa cells at N:P=20 in both serum-free and 10% serum-supplemented media (FIG. 20). The transfection efficiencies were calculated using the transfection efficiency of bPEI as 100%. The amino-β-CD$^+$:Ad-PVA complexes showed less than 20% transfection efficiency, with Method A complexes performing marginally better than Method B complexes. This low level of transfection is attributed to the formation of poorly internalized large aggregates that are formed due to the absence of sterically stabilizing PEG segments in this host:guest pendant polymer construct.

In the absence of serum, Method A amino-β-CD$^+$:Ad-PVA-PEG$_{750}$ complexes produced transfection efficiencies in the 15-55% range, depending on the amino-β-CD type, whereas complexes generated using Method B showed transfection efficiencies in the 10-25% range. In the presence of serum, complexes made from Ad-PVA-PEG$_{750}$ showed less than 10% efficiency. This can be attributed to the low serum stability of the particles due to the relatively low PEG density. Complexes made from Ad-PVA-PEG$_{2000}$ produced transfection efficiencies in the range of 40-140% of bPEI in the absence of serum and 30-130% of bPEI in the presence of serum. The presence of serum has little effect on the transfection efficiency of PEG$_{2000}$ constructs, due to the impact of either higher PEG MW or higher PEG loading on improved serum stability. Complexes made from the hydrazino-modified β-CD (6) and ethylenediamine-modified β-CD (5) showed better transfection efficiency than the ethanolamine (4) derivative. This finding is attributed to the lower charge density on these derivatives (due to the lower pK$_a$ expected for 6 and 4 relative to the 2° amines present on 5 that makes them capable of more facile exchange off the pDNA core).

The transfection experimental conditions used were those that had been previously optimized for bPEI in order to provide the comparison with this widely used transfection reagent. Note, however, that the performance of bPEI is also twofold lower and nearly 1000 times more toxic than the amino-β-CD$^+$:Ad-PVA-PEG$_{2000}$ complexes reported here (FIG. 19). Indeed, the widely reported dose-limiting toxicity of bPEI has been a major impediment to the further development of gene delivery strategies in vivo using this vector. In view of this limitation, the low toxicity of amino-β-CD$^+$:Ad-PVA-PEG complexes suggests that higher doses may be possible with this vector while still maintaining good cell viability.

Three other observations deserve note for the amino-β-CD$^+$:Ad-PVA-PEG complexes studied: (i) Method A complexes tend to produce higher transfection efficiencies than the analogous Method B complexes; (ii) Ad-PVA-PEG$_{2000}$ complexes were significantly more effective than Ad-PVA-PEG$_{750}$ complexes, which in turn were more effective than Ad-PVA complexes; and (iii) increased PEG loading and use of longer PEG results in complexes that are stable in the presence of serum. Smaller transfection complex sizes, improved solubility due to the presence of PEG, and improved steric stabilization are likely to be responsible for these findings. The smaller sizes of the transfection complexes may have led to an increase in the extent of cellular internalization of the particles, thereby leading to better transfection efficiencies for Method A. Conversely, the low solubility of the Ad-PVA complexes results in aggregation, giving rise to larger particles that may be too large to be effectively internalized, thus leading to lower transfection efficiencies.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A nucleic acid complex comprising a nucleic acid, a macrocyclic compound, and a pendant polymer, wherein the pendant polymer comprises a polymer backbone and is modified with a hydrophobic group, and wherein the macrocyclic compound and the pendant polymer form a host:guest polymer complex.

2. The nucleic acid complex of claim 1, wherein the nucleic acid is siRNA, miRNA, antisence oligonucleotides, aptamers, or pDNA.

3. The nucleic acid complex of claim 1, wherein the macrocyclic compound is a modified cyclodextrin.

4. The nucleic acid complex of claim 3, wherein the modified cyclodextrin is a modified β-cyclodextrin comprising an amino moiety.

5. The nucleic acid complex of claim 1, wherein the macrocyclic compound is
   mono-6-(amino)-6-deoxy-β-cyclodextrin,
   mono-6-(N,N'-dimethylethane-1,2-diamine)-6-deoxy-β-cyclodextrin,
   mono-6-(N'-(2-aminoethyl)ethane-1,2-diamine)-6-deoxy-β-cyclodextrin,
   mono-6-(poly(ethyleneimine)-6-deoxy-β-cyclodextrin
   hepta-6-(2'-aminoethyl)amino-β-cyclodextrin,
   hepta-6-(2'-hydroxyethylamino)-β-cyclodextrin, or
   hepta-6-(hydrazino)-β-cyclodextrin.

6. The nucleic acid complex of claim 1, wherein the pendant polymer comprises poly(vinyl alcohol), polysaccharide, polyester, or polyamide backbone.

7. The nucleic acid complex of claim 6, wherein the pendant polymer comprises a poly(ethylene glycol) pendant group.

8. The nucleic acid complex of claim 1, wherein the hydrophobic group is cholesterol, or a derivative or analog thereof, and wherein said cholesterol, or a derivative or analog thereof, is linked through an acetal linkage to the backbone of the pendant polymer.

9. The nucleic acid complex of claim 1, wherein the host:guest polymer complex condenses the nucleic acid to form a nanoparticle in a size of from about 120 nm to about 170 nm.

10. A method for delivering a nucleic acid into a cell, the method comprising the step of bringing a nucleic acid complex comprising the nucleic acid into contact with the cell, wherein the nucleic acid complex comprises a nucleic acid, a macrocyclic compound, and a pendant polymer, wherein the pendant polymer is modified with a hydrophobic group, and wherein the macrocyclic compound and the pendant polymer form a host:guest polymer complex.

11. The method of claim 10, wherein the nucleic acid is siRNA or pDNA.

12. The method of claim 10, wherein the macrocyclic compound is a modified cyclodextrin.

13. The method of claim 12, wherein the modified cyclodextrin is a modified β-cyclodextrin comprising an amino moiety.

14. The method of claim 10, wherein the macrocyclic compound is
   mono-6-(amino)-6-deoxy-β-cyclodextrin,
   mono-6-(N,N'-dimethylethane-1,2-diamine)-6-deoxy-β-cyclodextrin,
   mono-6-(N'-(2-aminoethyl)ethane-1,2-diamine)-6-deoxy-β-cyclodextrin,
   hepta-6-(2'-aminoethyl)amino-β-cyclodextrin,
   hepta-6-(2'-hydroxyethylamino)-β-cyclodextrin, or
   hepta-6-(hydrazino)-β-cyclodextrin.

15. The method of claim 10, wherein the pendant polymer comprises a poly(vinyl alcohol), polysaccharide, polyester, or polyamide backbone.

16. The method of claim 15, wherein the pendant polymer comprises a poly(ethylene glycol) pendant group.

17. The method of claim 10, wherein the hydrophobic group is cholesterol, or a derivative or analog thereof, and wherein said cholesterol, or a derivative or analog thereof, is linked through an acetal linkage to the backbone of the pendant polymer.

18. The method of claim 10, wherein the host:guest polymer complex condenses the nucleic acid to form a nanoparticle in a size of from about 120 nm to about 170 nm.

19. The method of claim 10, wherein said cell is in vitro or in vivo.

20. A pharmaceutical composition comprising the nucleic acid complex of claim 1 to produce a pharmaceutical for delivering a nucleic acid into a cell.

21. The nucleic acid complex of claim 1, wherein the hydrophobic group is adamantane, or a derivative or analog thereof, and wherein said adamantane, or a derivative or analog thereof, is linked through an acetal linkage to the backbone of the pendant polymer.

22. The method of claim 10, wherein the hydrophobic group is adamantane, or a derivative or analog thereof, and wherein said adamantane, or a derivative or analog thereof, is linked through an acetal linkage to the backbone of the pendant polymer.

* * * * *